(12) United States Patent
Paik et al.

(10) Patent No.: US 8,466,203 B2
(45) Date of Patent: Jun. 18, 2013

(54) METHOD OF STABILIZING HUMAN EYE TISSUE BY REACTION WITH NITRITE AND RELATED AGENTS SUCH AS NITRO COMPOUNDS

(76) Inventors: David Choohyun Paik, Cheltenham, PA (US); Stephen Lewis Trokel, New York, NY (US)

( * ) Notice: Subject to any disclaimer, the term of this patent is extended or adjusted under 35 U.S.C. 154(b) by 560 days.

(21) Appl. No.: 12/517,382

(22) PCT Filed: Dec. 6, 2007

(86) PCT No.: PCT/US2007/025126
§ 371 (c)(1),
(2), (4) Date: Nov. 10, 2009

(87) PCT Pub. No.: WO2008/070185
PCT Pub. Date: Jun. 12, 2008

(65) Prior Publication Data
US 2010/0173019 A1    Jul. 8, 2010

Related U.S. Application Data

(60) Provisional application No. 60/873,353, filed on Dec. 6, 2006, provisional application No. 60/936,635, filed on Jun. 20, 2007.

(51) Int. Cl.
*A01N 59/00* (2006.01)
*A01N 33/18* (2006.01)
*A01N 33/24* (2006.01)
*A61K 33/00* (2006.01)
*A61K 31/045* (2006.01)
*C12N 5/00* (2006.01)
*C12N 5/02* (2006.01)

(52) U.S. Cl.
USPC .......................................................... 514/727

(58) Field of Classification Search
USPC ............................ 424/718; 435/325; 514/727
See application file for complete search history.

(56) References Cited

U.S. PATENT DOCUMENTS
4,978,352 A * 12/1990 Fedorov et al. ................ 606/166

OTHER PUBLICATIONS

Eberhard Spoerl, et al, Induction of Cross-Links in Corneal Tissue, 66 Exp. Eye Res. 97 (1998).*
David C. Paik, et al, The Nitrite/Collagen Reaction: Non-Enzymatic Nitration as a Model System for Age-Related Damage, 42 Conn. Tiss. Res. 111 (2001).*

* cited by examiner

*Primary Examiner* — Sean Basquill
(74) *Attorney, Agent, or Firm* — Caesar, Rivise, Bernstein, Cohen & Pokotilow, Ltd.

(57) ABSTRACT

A method for stabilizing collagenous eye tissues by nitrite and nitroalcohol treatment. The topical stiffening agent contains sodium nitrite or a nitroalcohol in a buffered balanced salt solution and can be applied to the surface of the eye on a daily basis for a prolonged period. Application of the solution results in progressive stabilization of the corneal and scleral tissues through non-enzymatic cross-linking of collagen fibers. The compounds can penetrate into the corneal stroma without the need to remove the corneal epithelium. In addition, ultraviolet light is not needed to activate the cross-linking process. The resulting stabilization of corneal and scleral tissues can prevent future alterations in corneal curvature and has utility in diseases such as keratoconus, keratectasia, progressive myopia, and glaucoma.

18 Claims, 25 Drawing Sheets

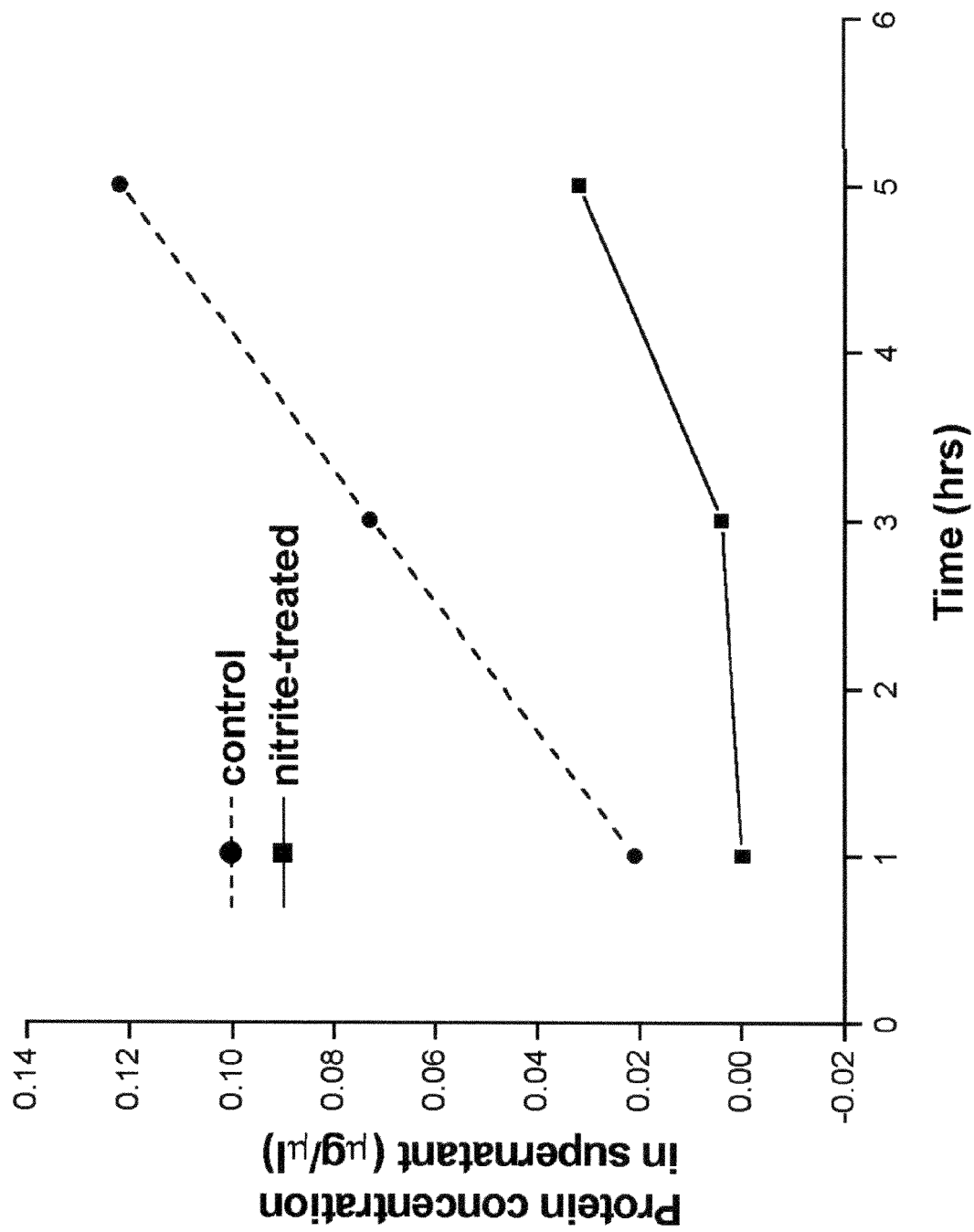

Example of Ts changes in cross-linked porcine sclera

Corneal transparency is preserved following cross-linking with β-nitro alcohols

Figure 15
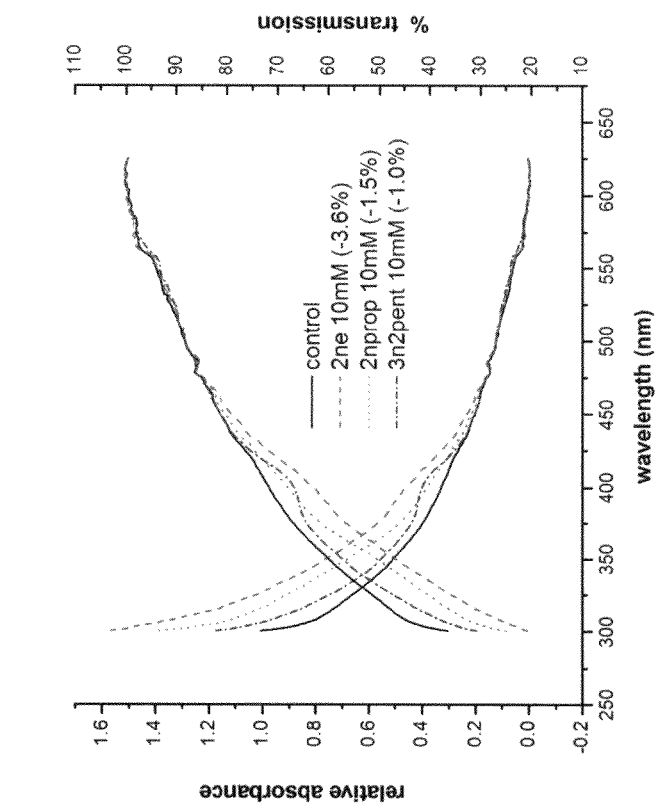
Absorbance/transmission curves
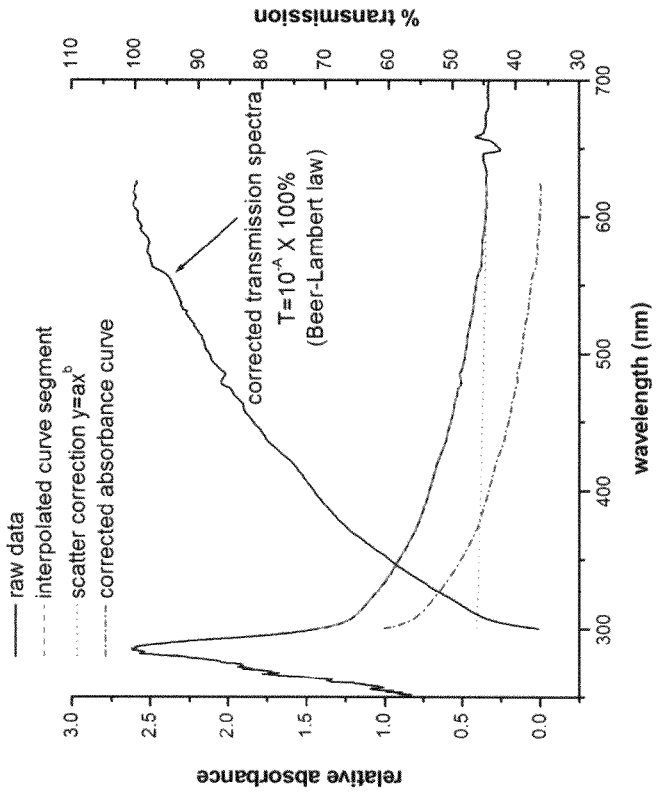
Sample of the analysis Thermal shrinkage is increased in porcine cornea through cross-linking by β-nitro alcohols Concentration dependent effects on shrinkage temperature curves by four different β-nitro alcohols Figure 23
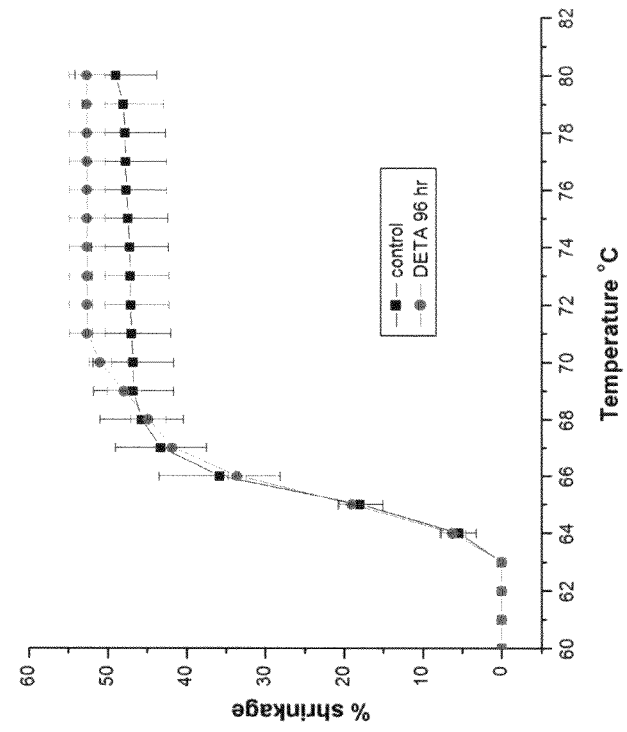
B
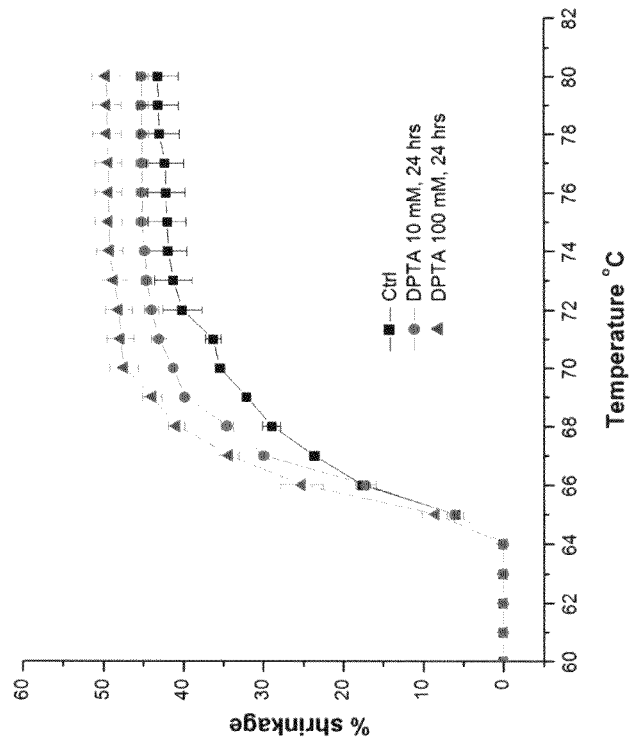
A

METHOD OF STABILIZING HUMAN EYE TISSUE BY REACTION WITH NITRITE AND RELATED AGENTS SUCH AS NITRO COMPOUNDS

This invention was made with support under United States Government Grant Nos. K08 AG00863 and R01 HL075639 from the National Institutes of Health. Accordingly, the United States government has certain rights in the subject invention.

Throughout this application various publications are referenced. The disclosures of these documents in their entireties are hereby incorporated by reference into this application in order to more fully describe the state of the art to which this invention pertains.

BACKGROUND OF THE INVENTION

Collagen is a fundamental protein found in connective tissue in animals, and it is present in the cornea and sclera of the eye. Several eye disorders are related to defects in collagen structure and include keratoconus, keratectasia, progressive myopia, and possibly glaucoma.

Keratoconus is a debilitating, progressive eye disorder, which is believed to occur due to progressive slippage of collagen lamellae in the cornea, usually bilateral, beginning between ages 10 and 20. The cornea develops a conical shape, causing significant changes in the refractive power of the eye. While corrective lenses may help vision, corneal transplant surgery may be necessary if eyeglasses or contact lenses are inadequate. THE MERCK MANUAL OF DIAGNOSIS AND THERAPY 722 (Mark H. Beers and Robert Berkow eds., 17th ed. 1999).

Keratoconus is estimated to affect 1 person in about 435 to 2000 people in the general population. In its classical form, keratoconus commences at puberty and progresses into the third to fourth decade of life Rabinowitz, Y. S., "Keratoconus," *Surv. Opthal.* 1998; 43(4):297-319. Thus, its overall impact is magnified by virtue of the younger population that it afflicts. Clinically, the disease is marked by progressive thinning of the corneal stroma with resultant bulging and distortion of the thinned, weakened areas. This thinning and distortion is documented by optical and ultrasonic methods. The bulging, distorted cornea creates an optically imperfect surface to the eye that produces an increasingly irregular astigmatism and myopia. Contact lenses are used to correct these optical imperfections when spectacle lenses are no longer able to compensate for the induced optical distortion. When contact lens correction fails, only a corneal transplant will allow restoration of visual function. The need for corneal transplantation arises when the disease has progressed and central corneal scar formation occurs, or the distortion is so great that contact lenses can no longer be worn.

Although the underlying etiology of keratoconus remains unclear, there are two main mechanistic theories currently entertained. The first is related to destabilization of collagen lamellae through increased degradation via imbalances in endogenous proteases and/or their inhibitors. In this regard, the scientific evidence has been somewhat equivocal with some studies showing increased matrix-metalloproteinase activity and others reporting no change (reviewed by Collier, S. A., "Is the corneal degradation in keratoconus caused by matrix-metalloproteinases?" *Clin. Exp. Opthalmol.* 2001; 29:340-344). An alternative theory regards collagen fibril slippage with no overall tissue loss. Meek, K. M., et al. have shown, using synchrotron X-ray scattering, that stromal lamellar organization is altered with an associated uneven distribution of collagen fibrillar mass. These changes are consistent with inter- and/or intra-lamellar slippage within the stromal layers of the keratoconic cornea, leading to central thinning. Meek, K. M., et al., "Changes in collagen orientation and distribution in keratoconus corneas," IOVS 2005; 46(6):1948-1956. The defect that would allow such slippage could be related to changes in the collagen to proteoglycan interactions and/or qualitative changes in the fibrillar collagens. Regarding this second point, very little is known about the qualitative biochemical collagen changes that occur in keratoconus. However, alterations in difunctional collagen cross-linking were reported decades ago. Cannon, J. and Foster, C. S., "Collagen crosslinking in keratoconus," IOVS 1978; 17(1):63-65; Oxlund, H. and Simonsen, A. H., "Biochemical studies of normal and keratoconus corneas," 1985; 63:666-669; Critchfield, J. W., et al., "Keratoconus: I. biochemical studies," *Exp. Eye Res.* 1988; 46:953-963. Regardless of the exact mechanism responsible for progressive corneal thinning, the pathologic changes that take place are accompanied by a loss of biomechanical strength. In this regard it has been shown that keratoconic corneas show a decreased stress for a given strain as compared to controls (i.e., decreased tissue stiffness) [Andreassen, T. T., et al., "Biomechanical properties of keratoconus and normal corneas," *Exp. Eye Res.* 1980; 31:435-441.] Andreassen, T. T., et al. also found that keratoconus collagen displayed a decreased resistance to enzymatic digestion with pepsin, a finding which is consistent with alterations in collagen cross-linking.

Current treatments for keratoconus either mask the surface irregularity with a variety of contact lenses, or attempt to improve the surface contour with intracorneal ring segments, lamellar keratoplasty, or excimer laser surgery. Binder, P. S., et al., "Keratoconus and corneal ectasia after LASIK," *J. Refract. Surg.* 2005; 21:749-752. However, the disease is progressive and none of these options obviates the need for eventual corneal transplantation.

Glaucoma is a group of disorders characterized by progressive damage to the eye at least partly due to increased intraocular pressure, the aqueous pressure in the eye. Increased intraocular pressure results from an inadequate aqueous outflow from the eye due to an obstruction in the trabecular meshwork from which the eye drains. Collagen is necessary to maintain the structural integrity of the trabecular meshwork. Rehnberg, M., et al., "Collagen distribution in the lamina cribosa and the trabecular meshwork of the human eye." *Brit. J. Opthalmol.* 71:886-92 (1987). Open-angle glaucoma can be treated with medical, laser, or surgical therapy to prevent damage to the optic nerve and visual field by stabilizing the intraocular pressure. THE MERCK MANUAL OF DIAGNOSIS AND THERAPY 733-36 (Mark H. Beers and Robert Berkow eds., 17th ed. 1999).

In myopia, or nearsightedness, the image of a distant object is focused in front of the retina because the axis of the eyeball is too long or the refractory power of the eye is too strong. Rays of light fall in front of the retina because the cornea is too steep or the axial length of the eye is too long. Without glasses, distant images are blurry, but near objects can be seen clearly. While glasses or contact lenses correct vision, refractive surgery decreases a patient's dependence on glasses or contact lenses. Progressive myopia is a condition associated with high refractive error and subnormal visual acuity after correction. This form of myopia gets progressively worse over time. THE MERCK MANUAL OF DIAGNOSIS AND THERAPY 741-43 (Mark H. Beers and Robert Berkow eds., 17th ed. 1999). The development of severe myopia is associated with scleral thinning and changes in the diameter of scleral collagen fibrils in humans. McBrien, N. A., et al., "Structural and Ultrastructural Changes to the Sclera in a Mammalian Model of High Myopia." *Investigative Opthalmol. & Visual Sci.* 42:2179-87 (2001).

Refractive surgery alters the curvature of the cornea to allow light rays to come to focus closer to the retina, thus improving uncorrected vision. In myopia, the central corneal curvature is flattened. However, ideal candidates for refractive surgery are people with healthy eyes who are not satisfied wearing glasses or contact lenses for their daily or recreational activities. Candidates for refractive surgery should not have a history of collagen vascular disease because of potential problems with wound healing. As keratoconus is a progressive thinning of the cornea, thinning the cornea further with refractive surgery may contribute to the advancement of the disease. Huang, X., et al., "Research of corneal ectasia following laser in-situ keratomileusis in rabbits." *Yan Ke Xue Bao,* 18(2):119-22 (2002). The side effects of refractive surgery include temporary foreign-body sensation, glare, and halos. Potential complications include over- and undercorrection, infection, irregular astigmatism, and, in excimer laser procedures, haze formation. Permanent changes in the central cornea caused by infection, irregular astigmatism, or haze formation could result in a loss of best corrected acuity.

Keratectasia is the protrusion of a thinned, scarred cornea. In laser in situ keratomileusis (LASIK), if the laser removes too much tissue, or the flap is made too deep, the cornea can become weak and distorted, leading to keratectasia. LASIK is contraindicated for patients with thin corneas, or those with keratectasia as a result of a prior LASIK procedure. Rigid gas permeable contact lenses are the recommended treatment for correcting vision in these patients. Kim, H., et al., "Keratectasia after Laser in situ Keratomileusis." *Int'l. J. Opthalmol.* 220:58-64 (2006).

A major breakthrough in the treatment of keratoconus and related keratectasias has been realized. Recent work by the German group of Wollensak, Spoerl, and Seiler has shown that cross-linking corneal collagen through application of riboflavin and ultraviolet light (UVR) can limit progressive vision loss in keratoconus patients. This modality represents a method through which stabilization of the corneal collagen lamellae and has been shown to prevent the progressive thinning of the cornea and loss of vision observed in keratoconus patients. This treatment involves the serial applications of riboflavin (0.1%) onto a de-epithelialized human cornea followed by exposure of the riboflavin saturated tissue to ultraviolet radiation in a UVA-370 nanometer wavelength region, at 3 mW/cm$^2$ radiant energy. The patient is treated with antibiotic drops to prevent infection and oral pain medicine after the procedure. Literature accruing over the past 9 years has described the utility of photochemical cross-linking using UVA irradiation ($\lambda$max=370 nm) with riboflavin as a photosensitizer (UVR). The work of the German group of Wollensak, G., Spoerl, E., and Seiler T., has shown that this method of cross-linking the collagen within the corneal stroma has proven effective in limiting the progression of corneal thinning, distortion, and resulting optical degradation of the eye. Wollensak, G., et al., "Riboflavin/ultraviolet-A-induced collagen crosslinking for the treatment of keratoconus." *Am. J. Opthalmol.* 2003; 135:620-27. Despite these successes, the UVR therapy poses attendant risks, particularly related to ultraviolet irradiation. As such, this therapy has yet to gain FDA approval in the US.

Because riboflavin tissue penetration is limited by the corneal epithelium, it is necessary to remove the corneal epithelium by scraping prior to riboflavin application. Removal of the corneal epithelium exposes the cornea to a risk of infection and causes significant pain. In addition, keratocyte (Wollensak, G., et al., "T. keratocyte cytotoxicity of riboflavin/ UVA treatment in vitro." Eye, 18:718-22 (2004); Wollensak, G., et al., "Keratocyte apoptosis after corneal collagen cross-linking using riboflavin/UVA treatment." *Cornea,* 23(1):43-49 (2004)) and corneal endothelial cell toxicity (Wollensak, G., et al., "Corneal endothelial cytotoxicity of riboflavin/ UVA treatment in vitro." *Ophthalmic Res.,* 35:324-28 (2003)) can occur with application of riboflavin/UVA to the cornea. In a similar manner, application of this therapy to the posterior sclera has been reported to damage cells in the photoreceptor, outer nuclear, and retinal pigment epithelial layers (Wollensak, G., et al., "Cross-linking of scleral collagen in the rabbit using riboflavin and UVA." *Acta Opthalmologica Scandinavica,* 83:477-82 (2005).

Currently, clinical trials are ongoing in Europe (Caporossi, A., et al., "Parasurgical therapy for keratoconus by riboflavin-ultraviolet type A rays induced cross-linking of corneal collagen: Preliminary refractive results in an Italian study," *J. Cataract Refract. Surg.* 2006; 32:837-845; Wollensak, G., "Crosslinking treatment of progressive keratoconus: new hope," *Cur. Opin. Ophthal.* 2006; 17:356-360) with significant interest generated for initiating clinical trials in the United States. The early reports from this therapy are encouraging. After 5 years in the Dresden study, individuals who have undergone this treatment protocol have yet to show progression of their keratoconus. With these encouraging results, corneal cross-linking therapy is being extended to include patients with related disorders such as the ectasia that occurs following LASIK (Laser-Assisted In situ Keratomileusis) and PRK (Photorefractive Keratectomy) excimer refractive surgery (Binder, P. S., et al., 2005). These are devastating complications of keratorefractive surgery in today's clinical practice. Anecdotal reports have also emerged reporting the use of collagen cross-linking as an effective means to control difficult-to-treat corneal fungal infections and corneal melts.

Despite these successes, the UVR therapy poses attendant risks, particularly related to ultraviolet irradiation. As such, this therapy has encountered difficulty gaining FDA approval and is currently unavailable in the United States. Because free oxygen radical formation occurs with riboflavin photolysis (Baier, J., et al., "Singlet oxygen generation by UVA light exposure of endogenous photosensitizers," *Biophys. J.* 2006; 91:1452-1459), this cross-linking method has a negative impact on cell viability. Indeed, keratocyte (Wollensak, G., et al., 2004) and corneal endothelial cell toxicity (Wollensak, G., et al., 2003) does occur with application of this therapy to the cornea. As a result of such toxicity, it has been recommended that patients with particularly thin central corneas (<400 µm) not undergo this therapy since the depth of UVA penetration exposes the endothelial cells (which are vital to maintaining corneal clarity through water regulation) to toxic photochemical damage. Furthermore, the long-term risks of this photochemical exposure are not known. Secondly, deep tissue penetration by the riboflavin requires removal of the corneal epithelium, a procedure that increases morbidity and complications. This requires analgesics and antibiotics following the UVR cross-linking procedure.

A need in the art exists to develop a topical self-administered compound in order to produce a comparable degree of collagen cross-linking to the UVR therapy.

SUMMARY OF THE INVENTION

This invention provides a method of cross-linking collagen in a collagenous tissue of a subject in need thereof comprising contacting the collagenous tissue with an amount of a nitrogen oxide-containing compound effective to cross-link the collagen in the collagenous tissue.

This invention also provides a method of inhibiting loss of structural integrity of a collagenous tissue during transplantation related transport comprising contacting the collagenous tissue with an amount of a nitrogen oxide-containing compound effective to inhibit loss of structural integrity of the collagenous tissue.

This invention further provides a composition for ophthalmic administration comprising a nitrogen oxide-containing compound, sodium chloride, potassium chloride, calcium chloride dihydrate, magnesium chloride hexahydrate, sodium acetate trihydrate, sodium citrate dehydrate, and water.

Finally, this invention provides a method of altering the refractive power of a cornea comprising contacting the cornea with a nitrogen oxide-containing compound so as to effect cross-linking in the cornea and thereby alter the refractive power of the cornea.

BRIEF DESCRIPTION OF THE FIGURES

FIG. 1—Protein concentration of collagen from nitrite treated cells in supernatant (μg/μl).

Figure 14:
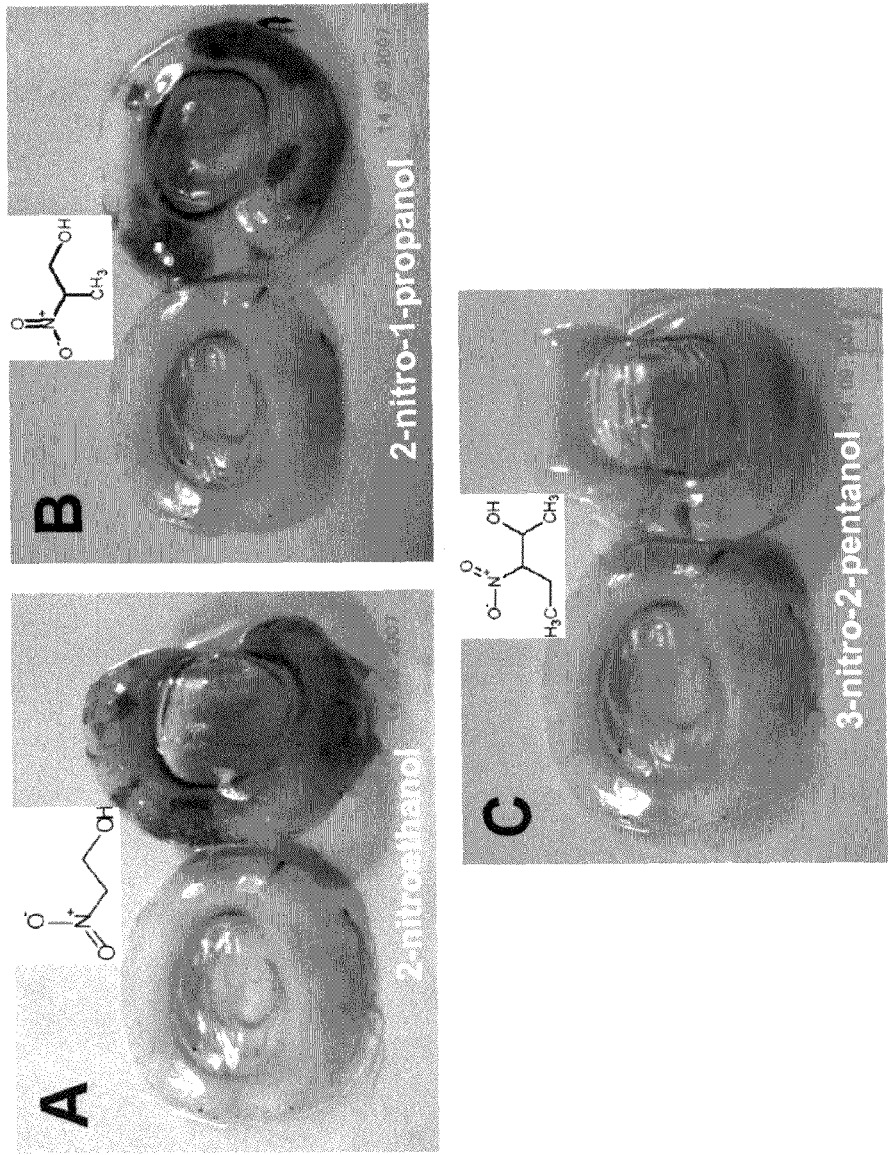

Fresh porcine corneal strips and corneoscleral complexes obtained within 6 hrs of sacrifice and incubated at 37° C. in buffered solutions (pH 7.4) containing 20% Dextran (T500) and either 100 mM NaNO2 or 100 mM of one each of the specified β-nitro alcohols
(A) 2-nitroethanol
(B) 2-nitro-1-propanol
(C) 3-nitro-2-pentanol
(D) NaNO2
(E) control FIG. 14—Corneal transparency is preserved following cross-linking with β-nitro alcohols.

Corneal tissue induced by reaction with 100 mM of
(A) 2-nitroethanol
(B) 2-nitro-1-propanol
(C) 3-nitro-2-pentanol
wherein, the sample mounted over the letter "C" is control and the sample mounted over the letter "N" is the specified β-nitro alcohol.

FIG. 15—Alterations in light transmission induced by corneal cross-linking with β-nitro alcohols.

Following a 96 hrs incubation period at 10 mM, corneoscleral complexes were mounted for measurement of absorbance spectra. Decreased transmission was greatest for 2-nitroethanol, followed by 2nprop, and 3n2pent. Integration of the 400-500 nm blue light region revealed decreases of 3.6%, 1.5%, and 1.0% respectively.
Sample of the Analysis and Absorbance/Transmission Curves FIG. 16—Thermal shrinkage is increased in porcine cornea through cross-linking by β-nitro alcohols.

Figure 17:
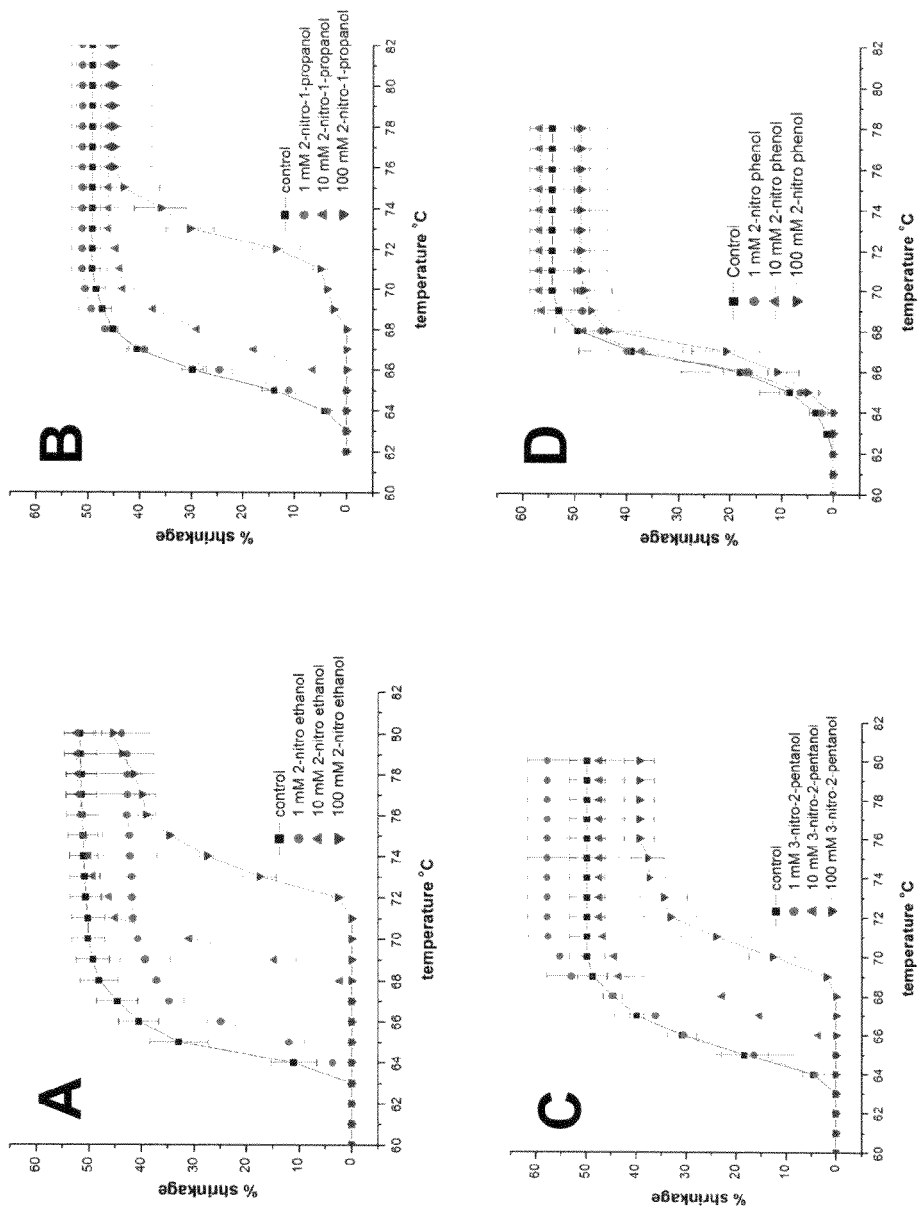

Specified β-nitro alcohols were serially applied over 6 days using various concentrations (1-100 mM)
(A) 2-nitroethanol
(B) 2-nitro-1-propanol
(C) 3-nitro-2-pentanol FIG. 17—Concentration dependent effects on shrinkage temperature curves by four different β-nitro alcohols.

Following 96 hrs of incubation at 37° C. using various concentrations of the specified β-nitro alcohols (1-100 mM), thermal shrinkage temperature was determined.
(A) 2-nitroethanol
(B) 2-nitro-1-propanol
(C) 3-nitro-2-pentanol
(D) 2-nitrophenol FIG. 18—Concentration dependent shift in $T_s$ of human sclera using 2-nitroethanol.

Following a 96 hrs incubation using various concentrations of 2-nitroethanol (1-100 mM), $T_s$ was determined. $T_{50}$ was shifted 0.3, 2.2, and 7.5° C. using 1, 10, and 100 mM 2-nitroethanol, respectively. The concentration dependent effect observed was similar to that observed using porcine sclera as in (B), which is the same graph shown as FIG. 18A (included for comparison purposes).
(A) Human
(B) Porcine FIG. 19—Time dependent shift in $T_s$ using 2-nitroethanol at 100 mM and 1 mM.
100 mM 2-nitroethanol Time of incubation was varied from 24 to 96 hrs. A time dependent effect in thermal shrinkage temperature shift was noted for 2-nitroethanol at 100 mM concentration over the course of 96 hrs with $T_{50}$ shifts of 1.4, 2.4, 5.3, and 7.7° C. for 24, 48, 72, and 96 hrs of incubation, respectively.
(B) 1 mM 2-nitroethanol Time dependent shift in $T_s$ using 2-2-nitroethanol at 1 mM. Conditions were as in (A) except that the time of incubation was varied from 0 to 14 days using a concentration of 1 mM. In addition, the incubation solution was "exchanged daily"

using a 1 mM solution of 2-nitroethanol. A time dependent shift in $T_s$ was noted for 2-nitroethanol at 1 mM concentration over the course of 14 days. $T_{50}$ was shifted 1.3, 3.2, and 5.6° C. for 6, 10 and 14 days of incubation, respectively. The shift in $T_s$ was commensurate to the shift observed using higher concentrations of 2-nitroethanol (i.e. 10 and 100 mM) for shorter durations (i.e. 24-96 hrs) [see FIG. 18A].

Figure 20:
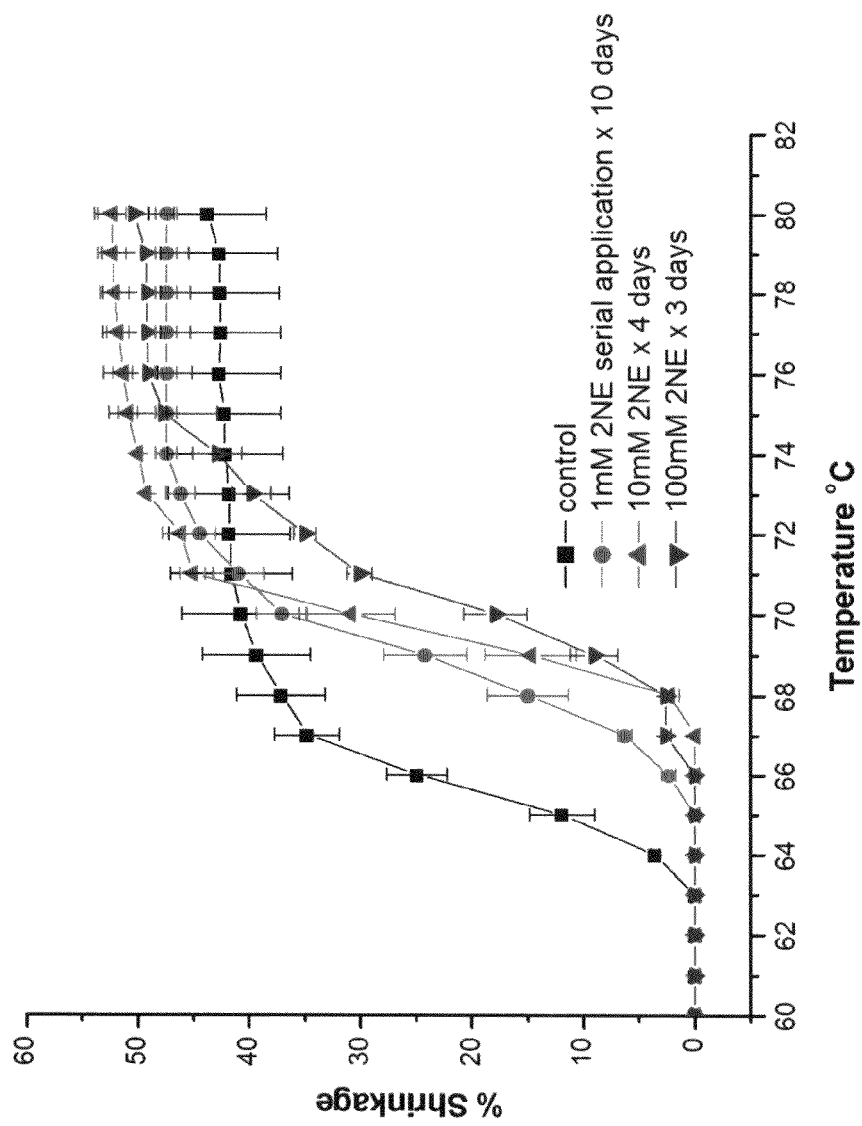

FIG. 20—Degrees of crosslinking through modulation of reagent concentration and time of exposure.

1 mM 2-nitroethanol concentration, the incubation solution was changed daily over the course of 10 days and compared to Ts changes produced through incubating with 10 mM 2-nitroethanol over 4 days and 100 mM 2-nitroethanol over 3 days without changing the solution.

Figure 21:
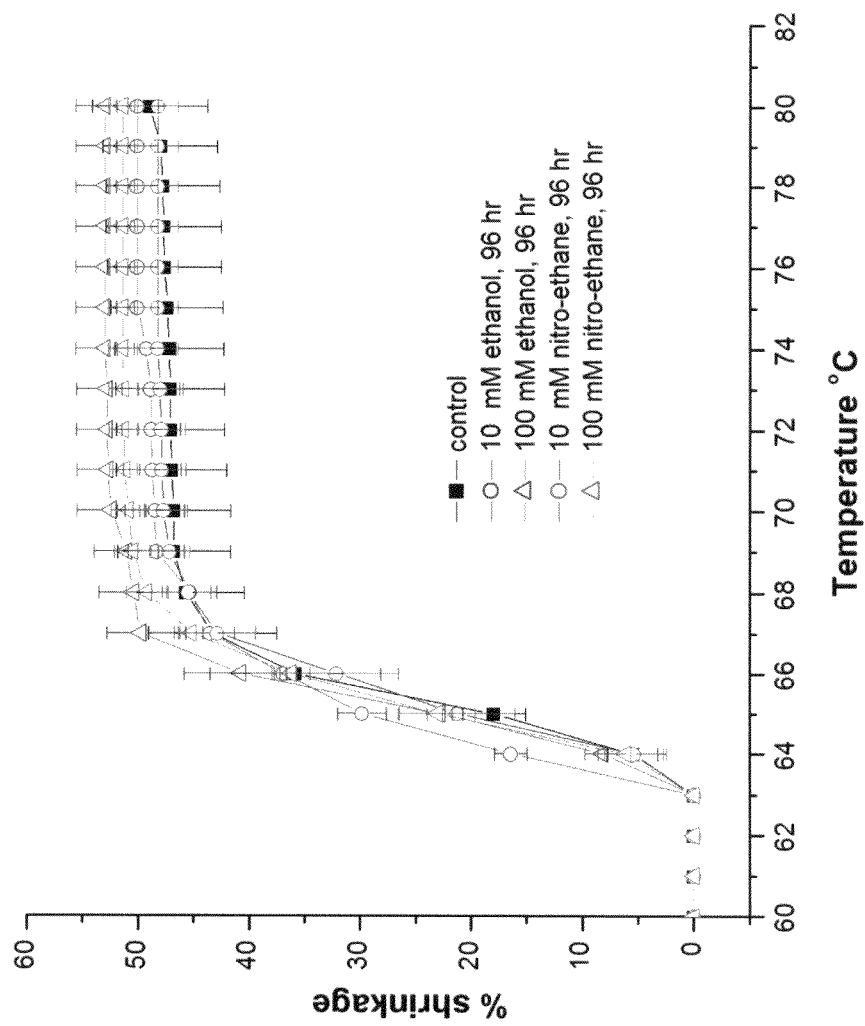

FIG. 21—Shrinkage temperature curve changes using nitro-ethane.

Figure 22:
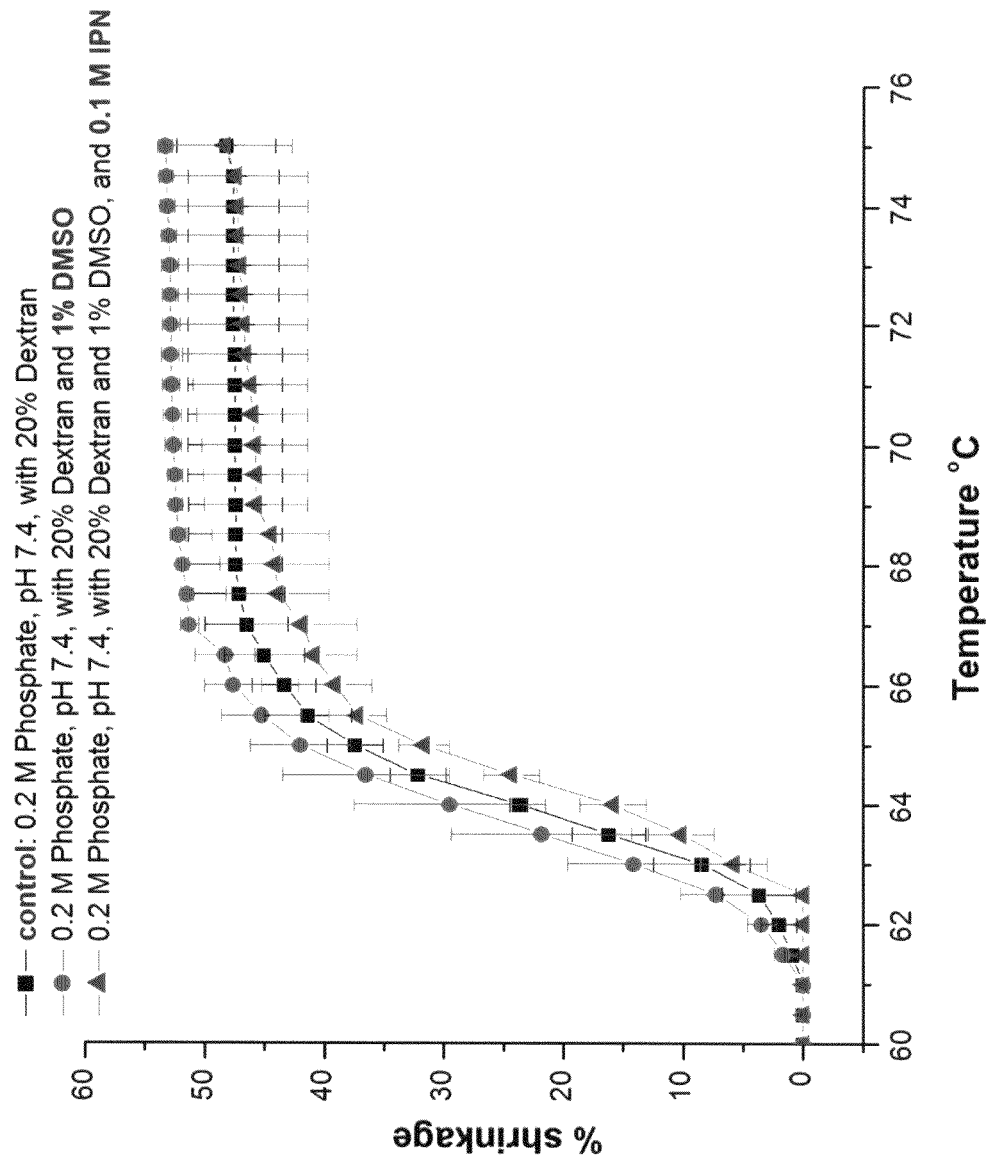

FIG. 22—Shrinkage temperature curve changes using isopentyl nitrite on porcine sclera.

FIG. 23—Shrinkage temperature curve changes using DPTA and DETA on porcine sclera.

Figure 24:
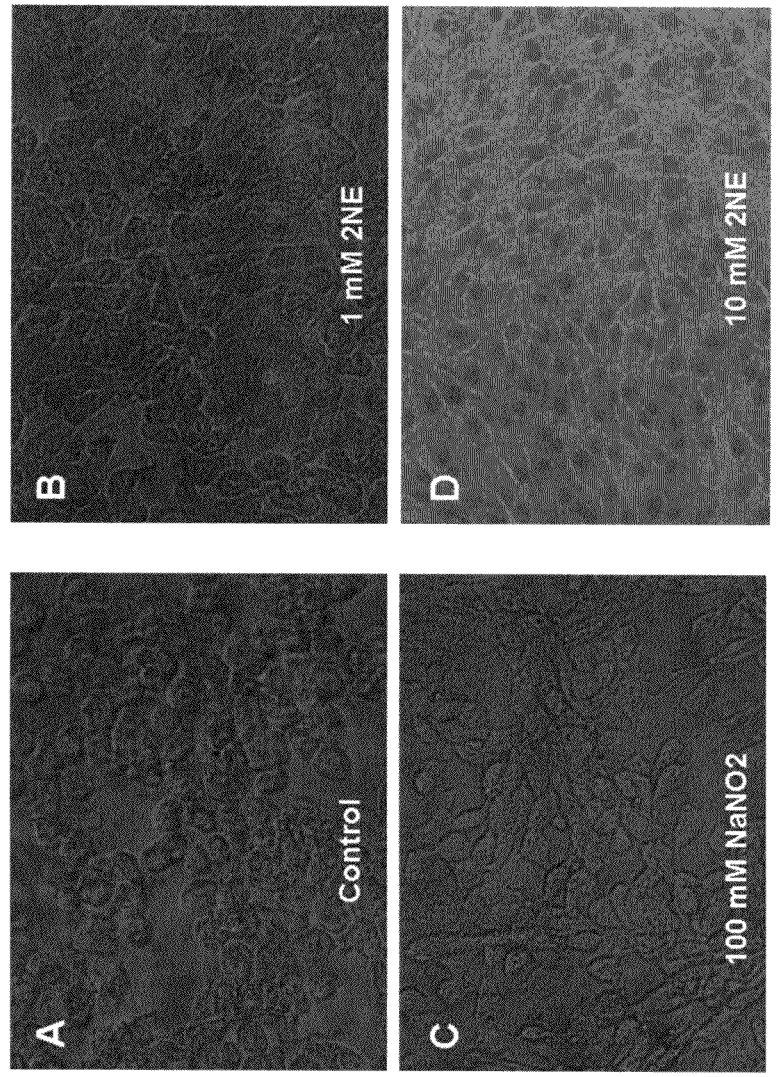

FIG. 24—Initial toxicity studies using ARPE-19 (24 hour exposure).
(A) Control
(B) 1 mM 2-nitroethanol
(C) 100 mM NaNO$_2$
(D) 10 mM 2-nitroethanol.

Figure 25:
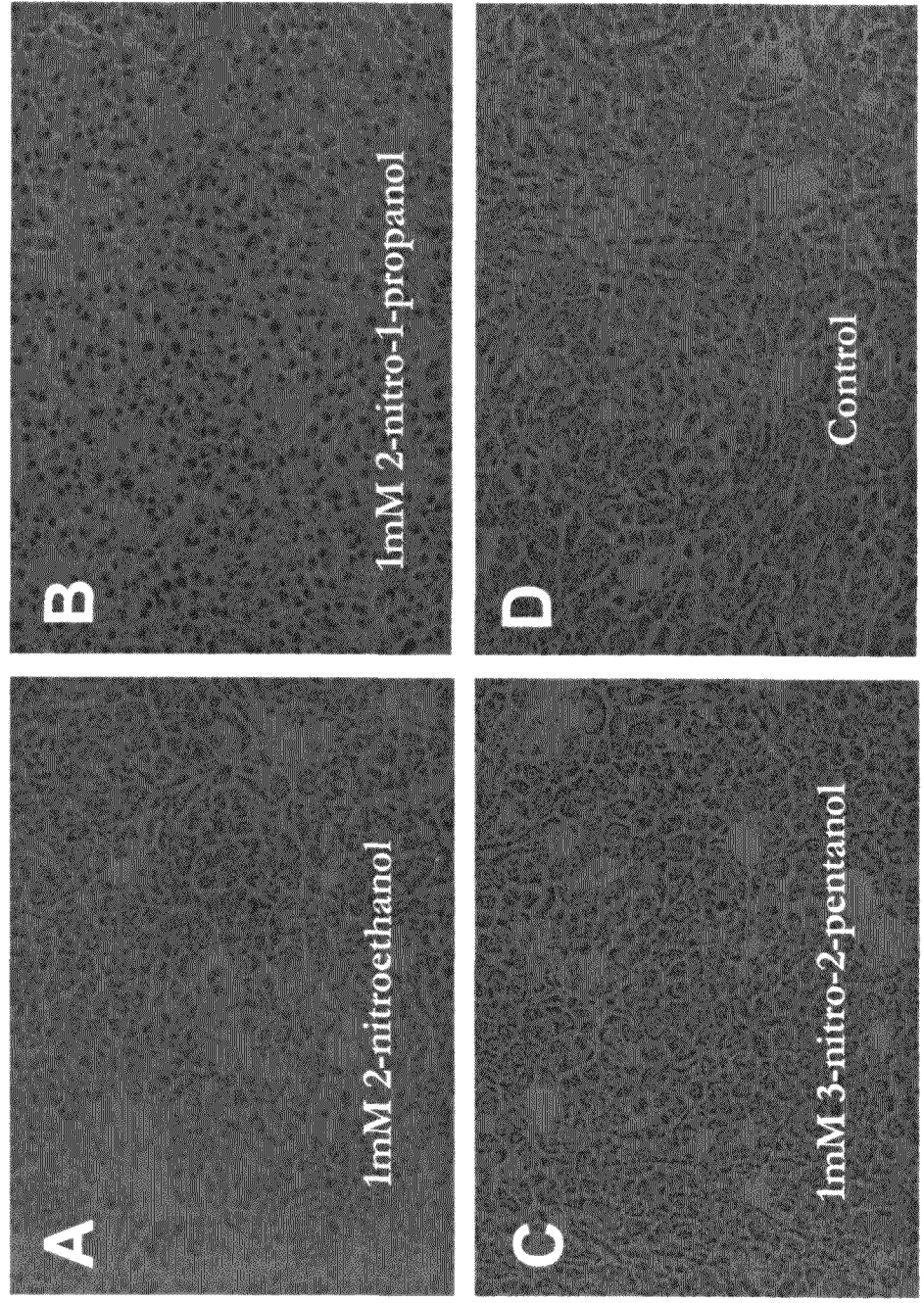

FIG. 25—Toxicity levels vary between β-nitro alcohols Toxicity studies in primary cultures of bovine corneal endothelial cells.
(A) 1 mM 2-nitroethanol
(B) 1 mM 2-nitro-1-propanol
(C) 1 mM 3-nitro-2-pentanol
(D) Control

DETAILED DESCRIPTION OF THE INVENTION

This invention provides a method of cross-linking collagen in a collagenous tissue comprising contacting the collagenous tissue with an amount of a nitrogen oxide-containing compound effective to cross-link the collagen in the collagenous tissue. In one embodiment, the collagenous tissue is cornea, sclera, or skin.

In one embodiment of the invention, the collagenous tissue is in a subject. In a preferred embodiment, the collagenous tissue is cornea and the subject is afflicted with keratoconus or keratectasia.

In various embodiments, the subject is a mammal, for example, a rabbit, a pig, a rat, or a primate, such as a human.

In an embodiment, the nitrogen oxide-containing compound is sodium nitrite or potassium nitrite. In another embodiment, the nitrogen oxide-containing compound is a β-nitro alcohol. The β-nitro alcohol may be 2-nitroethanol, 2-nitro-1-propanol, 2-nitro-1-pentanol, or 3-nitro-2-pentanol.

In one embodiment, the nitrogen oxide-containing compound is in an aqueous solution having a pH value of 3 to 8. In a specific embodiment, the aqueous solution has a pH value of 7.4. In another embodiment, the aqueous solution has a pH value of 5.0. By pH value of 3 to 8, it is meant that all hundredth, tenth and integer unit amounts within the range are specifically disclosed as part of the invention. Thus, 3.01, 3.02 . . . 7.98, 7.99; 3.1, 3.2 . . . 7.8, 7.9; and 4, 5 . . . 6, 7 pH values are included as embodiments of this invention.

In one embodiment, the nitrogen oxide-containing compound is in an aqueous solution of sodium phosphate, potassium phosphate, dextran, sodium chloride, potassium chloride, calcium chloride dehydrate, magnesium chloride hexahydrate, sodium acetate trihydrate, sodium citrate dehydrate, and balance water. In one embodiment, the nitrogen oxide-containing compound is in an aqueous solution of 0 percent to 20 percent sodium chloride by weight/volume, 0 percent to 20 percent postassium chloride by weight/volume, 0 percent to 20 percent sodium phosphate by weight/volume, 0 percent to 20 percent potassium phosphate by weight/volume, 0 to 20 percent dextran by weight/volume, 0 percent to 10 percent calcium chloride dihydrate by weight/volume, 0 percent to 10 percent magnesium chloride hexahydrate by weight/volume, 0 percent to 10 percent sodium acetate trihydrate by weight/volume, 0 percent to 10 percent sodium citrate dihydrate by weight/volume, 0 percent to 3 percent sodium hydroxide by weight/volume, 0 percent to 3 percent hydrochloric acid by weight/volume, and 0 to 90 percent deionized by weight/volume, and balance deionized, distilled water. In a specific embodiment, the nitrogen oxide-containing compound is in an aqueous solution of 0.50 percent to 1.00 percent sodium chloride by weight/volume, 0.01 percent to 1.00 percent postassium chloride by weight/volume, 0 percent to 10 percent calcium chloride dihydrate by weight/volume, 0 percent to 10 percent magnesium chloride hexahydrate by weight/volume, 0 percent to 10 percent sodium acetate trihydrate by weight/volume, 0 percent to 10 percent sodium citrate dihydrate by weight/volume, 0 percent to 1 percent sodium hydroxide by weight/volume, 0 percent to 1 percent hydrochloric acid by weight/volume, and 0 to 90 percent deionized, distilled water by weight/volume. In a specific embodiment, the nitrogen oxide-containing compound is in an aqueous solution of 0.64% sodium chloride by weight/volume, 0.075% potassium chloride by weight/volume, 0.048% calcium chloride dihydrate by weight/volume, 0.03% magnesium chloride hexahydrate by weight/volume, 0.39% sodium acetate trihydrate by weight/volume, 0.17% sodium citrate dehydrate by weight/volume, and balance deionized, distilled water. Examples of units of a compound in solution by weight/volume are mg/ml, g/100 ml, and kg/L. By percent of a compound in solution, it is meant that all hundredth, tenth and integer percentages within the range are specifically disclosed as part of the invention. Thus, 0.01, 0.02 . . . 99.98, 99.99; 0.1, 0.2 . . . 99.8, 99.9; and 1, 2 . . . 98, 99 percentages are included as embodiments of this invention.

In one embodiment of this invention the nitrogen oxide-containing compound is in a solution or solid comprising a transporter. In a further embodiment of this invention the transporter is taurine.

In various embodiments, the nitrogen oxide-containing compound is in an aqueous solution that can be administered to skin as a spray, low-viscosity aqueous liquid, alcoholic liquid, mist, aerosol, lotion, gel, cream, ointment, foam, paste, unguent, emulsion, liposomal suspension, colloid, cosmetic, foundation, moisturizer, sun-blocking agent, or combination thereof. In other embodiment, the aqueous solution may further comprise an antibiotic. In other embodiments, the aqueous solution may further comprise a fragrance. In one embodiment, the aqueous solution is suitable for administering to skin to prevent wrinkling.

In various embodiments, the tonicity of the aqueous solution is from 1 milli-osmoles to 100 osmoles.

In various embodiments, the contacting of the nitrogen oxide-containing compound to the collagenous tissue is performed by intermittent administration of the nitrogen oxide-containing compound to the collagenous tissue for a duration of time effective to cross-link collagen. In various embodiments, the solution is administered at intervals of one to ten times per day over a period of one day to one hundred and eighty days. In a specific embodiment, the solution is administered one to four times per day over a period of forty-two days. By administered one to ten times per day, it is meant that all integer unit amounts within the range are specifically disclosed as part of the invention. Thus, 2, 3, . . . 8, 9 administrations are included as embodiments of this invention. Similarly, the administration may be over a period of 2 days, 3 days . . . 178 days, or 179 days, and each integer value of days is included as an embodiment of this invention.

In one embodiment of this invention, the nitrogen oxide-containing compound is used in a field in which glutaraldehyde has been used to cross-link collagenous tissue. Examples of such fields include, but are not limited to, heart valves, bioprostheses, drug matrices, tanning leather, and fixing specimen. Nimni, M. E., "Glutaraldehyde fixation revisited," *Journal of Long-Term Effects of Medical Implants* 2001; 11(3&4):151-161; Jayakrishnan, A. and Jameela, S. R., "Review: Glutaraldehyde as a fixative in bioprostheses and drug delivery matrices," *Biomaterials* 1996; 17:471-484.

In one embodiment of this invention, the solution is administered as a composition selected from the group consisting of ophthalmic drops, ophthalmic salve, ophthalmic ointment, ophthalmic spray, subconjunctival injection, or intravitreal injection, contact lens, conjunctival insert, ocular time release insert, and sustained release implant. In a preferred embodiment, the solution is administered as an ophthalmic drop.

This invention also provides a method of inhibiting loss of structural integrity of a collagenous tissue during transplantation related transport comprising contacting the collagenous tissue with an amount of a nitrogen oxide-containing compound effective to inhibit loss of structural integrity of the collagenous tissue. In one embodiment, the collagenous tissue is contacted with the nitrogen oxide=containing compound before removal of the collagenous tissue from the donor subject. In another embodiment, the collagenous tissue is incubated during transport from the donor subject. In one embodiment, the nitrogen oxide-containing compound is nitrous acid. In one embodiment, the donor subject is a mammal, for example, a rabbit, a pig, a rat, or a primate. In a specific embodiment, the donor subject is a human. In another embodiment, the donor subject is a pig. In one embodiment, the collagenous tissue is a heart valve. In another embodiment, the collagenous tissue is skin. In yet another embodiment, the collagenous tissue is cornea. In one embodiment, the contacting is at a temperature greater than 60° C. In another embodiment, the contacting is at a temperature greater than 62° C.

This invention provides a composition for ophthalmic administration comprising a nitrogen oxide-containing compound, sodium phosphate, potassium phosphate, dextran, sodium chloride, potassium chloride, calcium chloride dihydrate, magnesium chloride hexahydrate, sodium acetate trihydrate, sodium citrate dehydrate, and water.

In one embodiment, the composition for ophthalmic administration comprising 0 to 100 percent of a nitrogen oxide-containing compound by weight/volume, 0 percent to 20 percent sodium phosphate by weight/volume, 0 percent to 20 percent potassium phosphate by weight/volume, 0 percent to 20 percent dextran by weight/volume, 0 percent to 20 percent sodium chloride by weight/volume, 0 percent to 20 percent postassium chloride by weight/volume, 0 percent to 10 percent calcium chloride dihydrate by weight/volume, 0 percent to 10 percent magnesium chloride hexahydrate by weight/volume, 0 percent to 10 percent sodium acetate trihydrate by weight/volume, 0 percent to 10 percent sodium citrate dihydrate by weight/volume, 0 percent to 3 percent sodium hydroxide by weight/volume, 0 percent to 3 percent hydrochloric acid by weight/volume, and 0 to 90 percent deionized by weight/volume, balance deionized, distilled water by weight/volume. In a specific embodiment, the composition for ophthalmic administration comprises 0 to 50 percent of a nitrogen oxide-containing compound by weight/volume, 0 percent to 20 percent sodium phosphate by weight/volume, 0 percent to 20 percent potassium phosphate by weight/volume, 0 percent to 20 percent dextran by weight/volume, 0.50 percent to 1.00 percent sodium chloride by weight/volume, 0.01 percent to 1.00 percent postassium chloride by weight/volume, 0 percent to 10 percent calcium chloride dihydrate by weight/volume, 0 percent to 10 percent magnesium chloride hexahydrate by weight/volume, 0 percent to 10 percent sodium acetate trihydrate by weight/volume, 0 percent to 10 percent sodium citrate dihydrate by weight/volume, 0 percent to 1 percent sodium hydroxide by weight/volume, 0 percent to 1 percent hydrochloric acid by weight/volume, and 0 to 90 percent deionized, distilled water by weight/volume.

In a preferred embodiment, the composition for ophthalmic administration comprises a nitrogen oxide-containing compound, 0.64% sodium chloride by weight/volume, 0.075% potassium chloride by weight/volume, 0.048% calcium chloride dihydrate by weight/volume, 0.03% magnesium chloride hexahydrate by weight/volume, 0.39% sodium acetate trihydrate by weight/volume, 0.17% sodium citrate dehydrate by weight/volume, and balance deionized, distilled water.

In one embodiment, the composition has a pH of 3 to 8. In a specific embodiment, the composition has a pH of 7.4. In another embodiment, the composition has the tonicity of 1 milli-osmoles to 100 osmoles.

This invention provides a method of altering the refractive power of a cornea comprising contacting the cornea with a nitrogen oxide-containing compound so as to effect cross-linking in the cornea and thereby alter the refractive power of the cornea. In one embodiment the nitrogen oxide-containing compound is a β-nitro alcohol. In another embodiment the refractive power of the cornea is increased. In yet another embodiment the cross-linking effected in the cornea causes a surface contour of the cornea to change shape. In a further embodiment the cornea is an isolated cornea. In one embodiment the cornea is a porcine cornea. In another embodiment the cornea is a human cornea. In one embodiment the β-nitro alcohol is 2-nitroethanol. In another embodiment the β-nitro alcohol is 2-nitro-1-propanol. In one embodiment the β-nitro alcohol is 3-nitro-2-pentanol. In another embodiment the β-nitro alcohol is 2-nitro-1-pentanol.

As used herein, "nitrogen oxide-containing compound" refers to any chemical compound that contains at least one nitrogen oxide functional group. Nitrogen oxide-containing compounds include, but are not limited to, nitrites of the general formula RONO, nitro compounds of the general formula $RNO_2$, nitroso compounds of the general formula RNO, and NONOates of the general formula RR'N—(NO—)—N=O, where R and R' can be any organic group, such as an acetal, acid anhydride, alcohol, aldehyde, alkane, cycloalkane, alkene, cycloalkene, alkyl, alkylamine, alkyl halide, alkyne, cycloalkyne, allyl, amide, amine, annulene, arene, aryl halide, arylamine, aryne, carbinolamine, carboxylic acid, dicarboxylic acid, hydrocarbon, imide, imine, lactam, lactone, peroxide, phenol, phenyl, polyamide, polyamine, polycyclic aromatic hydrocarbon, polycyclic hydrocarbon, saccharide, thiol, thioester, or a substituted group where the substitutent is any of the aforementioned groups.

Nitrite containing examples include, but are not limited to nitrous acid, sodium nitrite, and isopentyl nitrite. Specific nitrites shown to work in this invention include sodium nitrite and potassium nitrite. Some nitrites can be nitrosating agents as defined herein.

Examples of nitro compounds include, but are not limited to nitroalkanes and β-nitro alcohols. Specific nitro compounds shown to work in this invention include 2-nitroethanol, 2-nitro-1-propanol, and 2-nitro-1-pentanol.

Examples of nitroso compounds include, but are not limited to 2-methyl-2-nitrosopropane and methanamine. Some nitroso compounds can be nitrosating agents as defined herein.

Examples of NONOates include, but are not limited to, diethylamine NONOate and spermine NONOate.

As used herein, "nitrosating agent" refers to any chemical compound that can impart an NO group onto another molecule. The compound can be either an ionic or covalent compound, such as a salt or an ester of nitrous acid. Nitrites of the alkali and alkaline earth metals may be synthesized by reacting a mixture of nitric oxide and nitrogen dioxide with the corresponding metal hydroxide solution, as well as through the decomposition of the corresponding nitrate. Nitrites are also available through the reduction of the corresponding nitrates. In one embodiment, "nitrosating agent" refers to, but is not limited to, the group consisting of nitrous acid (as nitrosonium ion and/or dinitrogen trioxide); nitrosyl halides of the formula HalNO where Hal is fluorine, chlorine, bromine, iodine, or astatine; nitrosonium salts; alkyl nitrites; N-Nitrososulfonamides of the formula $RSO_2N(NO)R'$, where R and R' can be any organic substituent, such as an acetal, acid anhydride, alcohol, aldehyde, alkane, cycloalkane, alkene, cycloalkene, alkyl, alkylamine, alkyl halide, alkyne, cycloalkyne, allyl, amide, amine, annulene, arene, aryl halide, arylamine, aryne, carbinolamine, carboxylic acid, dicarboxylic acid, ether, hydrocarbon, imide, imine, ketone, lactam, lactone, peroxide, phenol, phenyl, polyamide, polyamine, polycyclic aromatic hydrocarbon, polycyclic hydrocarbon, saccharide, thiol, or thioester; tetranitromethane $C(NO_2)_4$; inorganic nitrates; nitrite with carbonyl group catalysts; nitrosyl carboxylates (acyl nitrites) of the formula RCOONO, where R has the same definition as previously disclosed; Fremy's salt $K_2[(SO_3)_2NO]$; and sulfur-nitroso compounds such as thionyl chloronitrite SOCIONO and thionyl dinitrite $SO(ONO)_2$. In a specific embodiment, "nitrosating agent" refers to the group consisting of sodium nitrite and potassium nitrite.

As used herein, "collagenous tissue" refers to any bodily tissue that contains the protein collagen, such as skin, blood vessels, heart valve, tendons, bone, cartilage, tendonous tissue, and eye tissues such as the cornea, sclera, and retina.

As used herein, "corneoscleral disorder" is any disease, condition, or abnormality of the cornea and/or scleral tissue of the eye involving a loss of stiffness and/or contour changes of the eye. Thus, the corneoscleral disorder may be keratoconus, keratectasia, progressive myopia, or glaucoma.

As used herein, "transporter" is any compound that allows passage of a nitrogen oxide-containing compound into the stroma. An example of a transporter includes, but is not limited to, taurine.

As used herein, "tonicity" refers to the ability of a solution to cause water movement. Tonicity is measured in osmoles, which is defined by the number of moles of a chemical compound that contribute to a solution's osmotic pressure. In various embodiments of this invention, the solution has a tonicity of between about 1 milli-osmoles and 100 osmoles. By tonicity of between about 1 milli-osmoles and 100 osmoles, it is meant that all hundredth, tenth and integer unit amounts within the range are specifically disclosed as part of the invention. Thus, 1.01, 1.02 ... 99.98, 99.99; 1.1, 1.2 ... 99.8, 99.9; and 2, 3 ... 98, 99 osmolar values are included as embodiments of this invention.

It is to be understood that the invention is not limited in its application to the details set forth in the description or as exemplified. The invention encompasses other embodiments and is capable of being practiced or carried out in various ways. Also, it is to be understood that the phraseology and terminology employed herein is for the purpose of description and should not be regarded as limiting.

EXAMPLES

Biaxial Mechanical Tests

Biaxial mechanical properties of the collagen gels were examined by performing equibiaxial load controlled experiments after 72 hours of culture for pretreated and 10 days of culture for posttreated collagen gels. To perform the planar biaxial mechanical test, the loading frame was first removed and the gels were floated to the top of their Petri dish using standard media (DMEM with 10% FBS and antibiotics) at 37° C. Gels were loaded by applying equal weights on all sides of the gel simultaneously (equibiaxial loading). First, gels were preconditioned by cyclically applying and removing 1 gram weights on all sides. Preconditioning refers to a standard phenomenon in soft biologic tissues where the response to an applied load differs with the first few applications but eventually stabilizes as the load is repeatedly applied and removed. In these gels we have found that five cycles are sufficient to obtain a stable response, so five cycles of preconditioning were applied to all gels. One prominent feature of the preconditioning response in these gels is that the gels undergo some permanent deformation, not relaxing back to their initial dimensions even when fully unloaded.

The magnitude of the permanent deformation associated with preconditioning was quantified by computing the associated strain ($E^P_{11}$, $E^P_{22}$) using the unloaded configuration of the gel at the beginning of the mechanical test as the reference state and the new, stable unloaded state achieved at the end of preconditioning as the deformed state. After preconditioning, calibrated weights from 0 to 1000 mg are applied equibiaxially in 100 mg increments. Images of the gel surface are taken 30 seconds after each load application or removal, and the strains associated with each load were computed relative to the preconditioned unloaded reference state at the beginning of the loading run.

Figure 4:
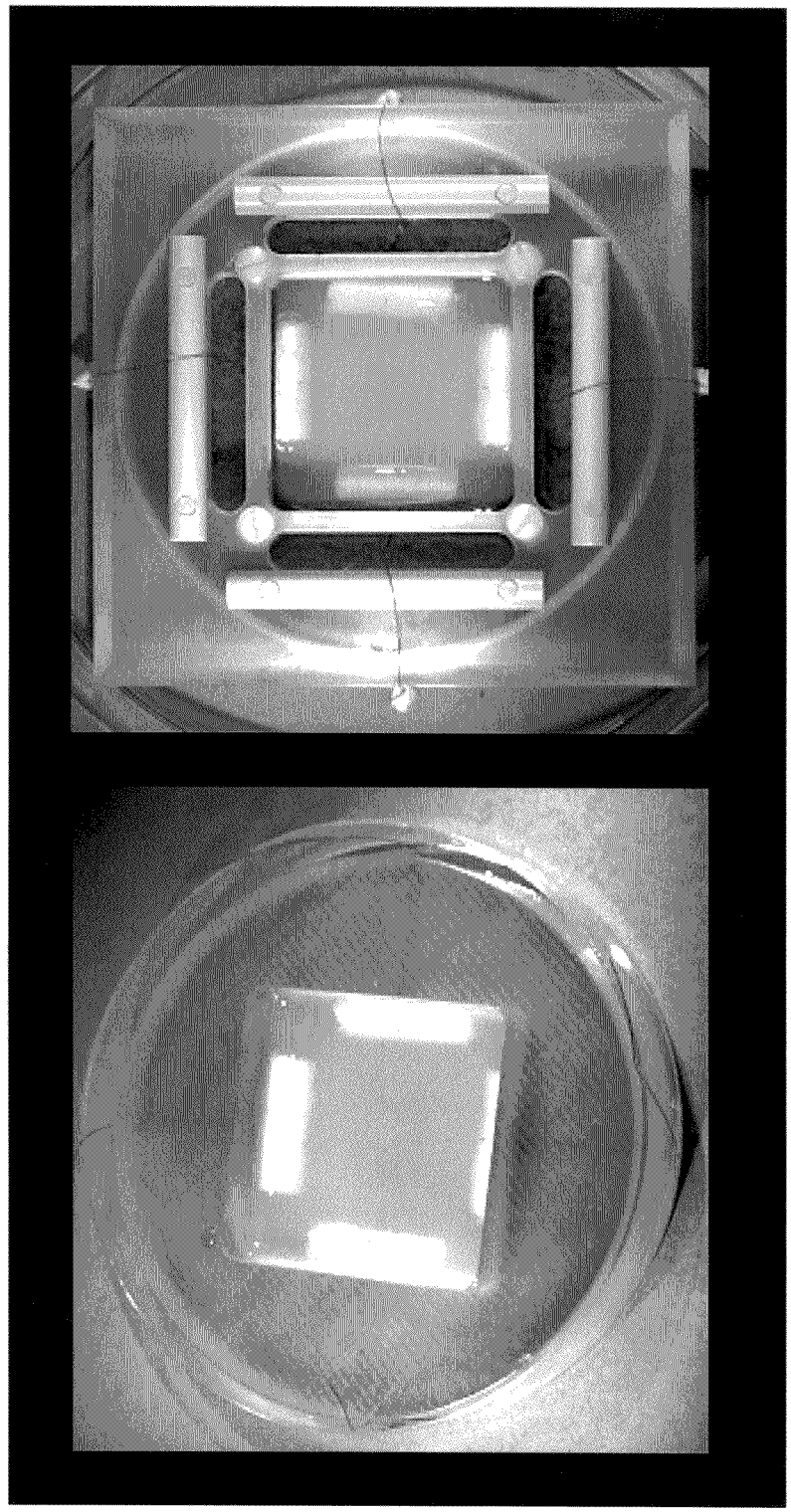
FIG. 4—Diagram and average deformation data showing the phases of the experiment for a uniaxially constrained gel.

A fibroblast-populated collagen gel model system was designed specifically for biaxial loading as seen in FIG. 4. Gel is poured into a square mold and allowed to polymerize into porous holding bars. During development in the incubator, isotonic uniaxial or biaxial loading conditions can be applied using weights. Unloaded gels contract to 30% of initial area by 72 hours (open symbols, n=3); contraction decreases with load (gray lines) until just detectable at 200 mg per side (closed symbols, n=3) of 4×4 cm squares.

Collagen Fiber Orientation

Collagen fiber structure was evaluated using confocal reflectance microscopy in gels fixed after mechanical testing. Gels were fixed in 3.7% formaldehyde in PBS for 24 hours and stored in PBS with 1% sodium azide at 4° C. Collagen was imaged using a 60× oil immersion objective and an argon laser (488 nm) on an Olympus Fluoview 1×70 confocal microscope. Digital images (1024×1024 pixel resolution) were then analyzed for structural information using a gradient detection algorithm. Because collagen is birefringent and confocal microscopy uses a polarized laser, an additional correction was made to remove the resulting bias in the apparent collagen fiber distributions. Four different fields in the central region of each gel were imaged with the vertical image axis aligned with the $x_1$ direction, then the gel was rotated 90° clockwise and four more fields in the central region were imaged. The collection of eight orientation histograms for each gel was then fitted with a sum of two distributions: a "fiber" distribution assumed to rotate with the gel and an "error" distribution assumed to remain stationary.

In the least squares fitting procedure, both distributions were modeled as cosine functions of the form $A+B \cos(\omega\theta - \phi)$. For the error distribution, all four parameters in this function were allowed to vary, while the frequency $\omega$ of the fiber distribution was fixed at 2 to reflect the natural periodicity of fiber distributions (i.e., a fiber oriented at 0° also can be said to be oriented at 180°, 360°, 540°, etc.).

Biochemical Analysis of Collagen Cross-Linking by SDS-PACE

Samples of pepsin-solubilized, bovine skin collagen type I (Purecol, 3 mg/ml, Inamed Corporation, Fremont, Calif., USA) dissolved in 0.012N HCl were spiked with $dH_2O$ containing 1M $NaNO_2$ or NaCl concentration to obtain final concentrations of 0 mM, 10 mM, 100 mM $NaNO_2$, and 100 mM NaCl. The addition of the spiking solution resulted in an increase in pH from 2.5 to 4.0 for the highest nitrite concentration. These conditions were identical to those used in the preincubation treatment of collagen for biomechanical testing. Following a 24 hour incubation (4° C.), an aliquot from each sample was added into SDS-PAGE sample buffer (Biorad) in a ratio of 1:2 (sample:sample buffer), reduced by heating at 100° C. for 5 minutes with dithiothreitol (DTT), and analyzed by SDS-PAGE. The separating gel was 5% acrylamide and stacking gel 4%. Equivalent quantities of protein (6 µg per lane) were loaded onto separate wells. The samples were run at 25 volts for approximately 3.5 hours, which was the time necessary for the dye front to leave the bottom of the gel. The gels were then stained with Coomasie blue solution for no less than 3 hours. Following destaining, the gels were digitally photographed for densitometric analysis, which was carried out using the Un-Scan-it software program version 4.1 (Silk Scientific Corp).

Collagen Treated By Nitrite

Example of Resistance of Nitrite-Treated Collagen to Digestion

FIG. 1 shows a quantitative protein assay of nitrite-treated collagen following digestion by collagenase. Insoluble type I collagen was incubated in 100 mM sodium nitrite or sodium chloride solutions for 8 weeks. The samples were then digested with bacterial collagenase (Sigma). Protein assay (Biorad) of solubilized protein in the supernatant fraction shows control collagen was digested more readily than nitrite-treated collagen at 1, 3, and 5 hours. At 7 and 12 hours, the solubilized fractions were acid hydrolyzed and quantitated by amino acid analysis. The results from the amino acid analysis were in agreement with these findings. Each point in FIG. 1 represents the average of two independent determinations.

Figure 2A:
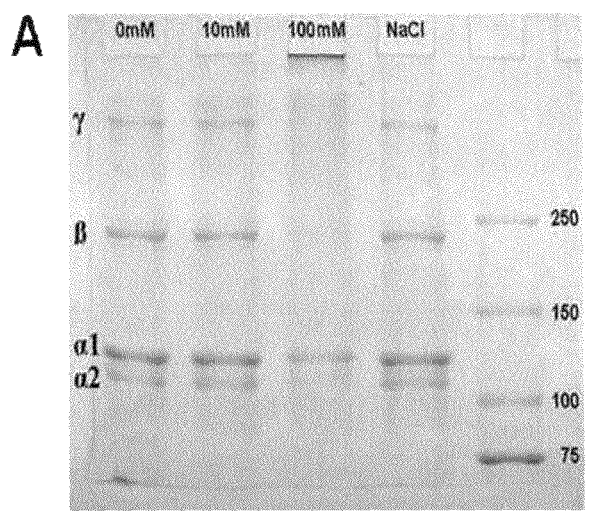
FIG. 2—(A) SDS-PAGE (5% separating gel) of post-treated type I collagen following a 7-day incubation (pH 7.4) with 0, 10, 100 mM NaNO2, and 100 mM NaCl, (B) Densitrometric analysis of FIG. 2(A) gel, (C) Biomechanical testing on fibroblast populated collagen type I gels.
Figure 2B:
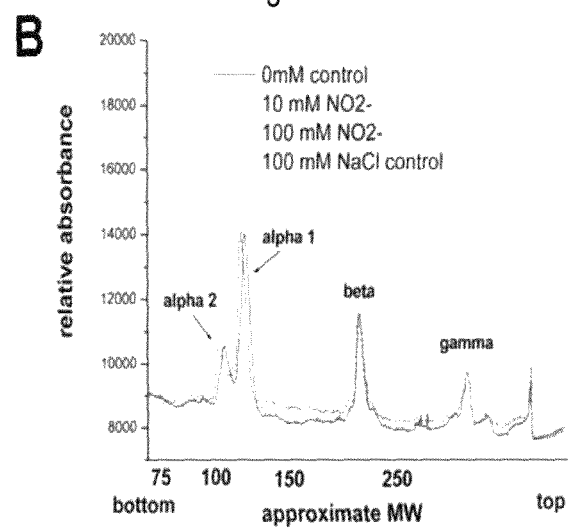
Figure 2C:
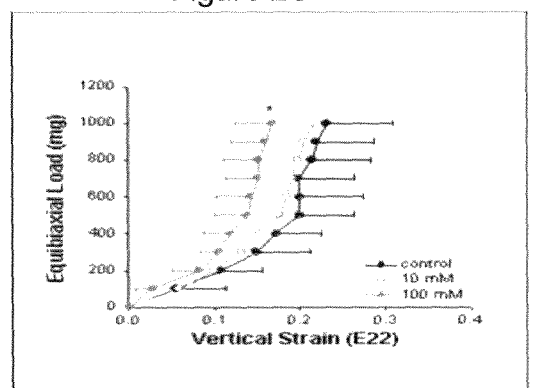

Example of Posttreated Type I Collagen at pH 7.4 Collagen Cross-Linking is Induced by Reaction with $NaNO_2$ The results of these studies indicate by SDS-PAGE that collagen cross-linking is induced by reaction with $NaNO_2$. FIG. 2(A) illustrates a SDS-PAGE (5% separating gel stained with Coomasie blue) of type I collagen (Purecol, Inamed Corp) following a 7 day incubation (1 mg/ml, pH 7.4, 4° C.) with 0, 10, 100 mM $NaNO_2$, and 100 mM NaCl. At 100 mM $NaNO_2$ cross-linking of collagen primary strands is indicated by the dark band at the top of the gel. These proteins were unable to enter even the stacking gel. This high molecular weight band has formed in conjunction with lesser amounts of lower molecular weight proteins (i.e. α-single chain, β-dimer, and γ-trimer bands) indicating the formation of cross-linked collagen strands by reaction with nitrite. No differences are observed between the unreacted control, 10 mM $NaNO_2$, and the 100 mM NaCl control. Standard ladder proteins are seen on the right. FIG. 2(B) shows a densitometric analysis of the FIG. 2(A) gel. The digital image from the top panel was scanned using Un-Scan-It software (version 4.1). A marked diminution of alpha, beta, and gamma bands in the high nitrite treated samples is noted with a sharp increase in protein unable to enter the gel. FIG. 2(C) shows biomechanical testing on fibroblast populated collagen type I gels.

Figure 5A:
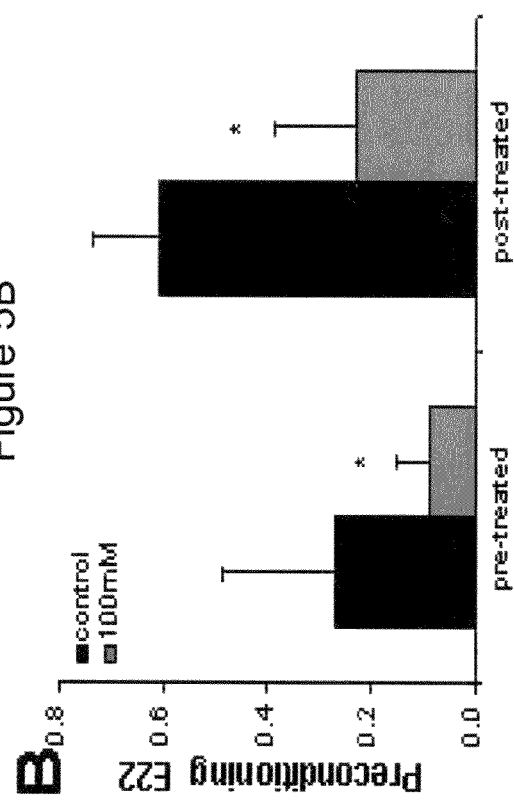
FIG. 5—Impact of sodium nitrite on vertical deformation of uniaxially constrained gels during each phase of the experiment.
(A) Pretreatment at pH 4.0 for 24 hours with 100 mM sodium nitrite and posttreatment at pH 7.4 for seven days with 100 mM sodium nitrite both reduced vertical remodeling;
(B) Pretreatment at pH 4.0 for 24 hours with 100 mM sodium nitrite and posttreatment at pH 7.4 for seven days with 100 mM sodium nitrite both reduced vertical deformation associated with preconditioning; and
(C) Pretreatment at pH 4.0 for 24 hours with 100 mM sodium nitrite and posttreatment at pH 7.4 for seven days with 100 mM sodium nitrite both reduced vertical deformation at 1 g equibiaxial load.
Figure 5B:
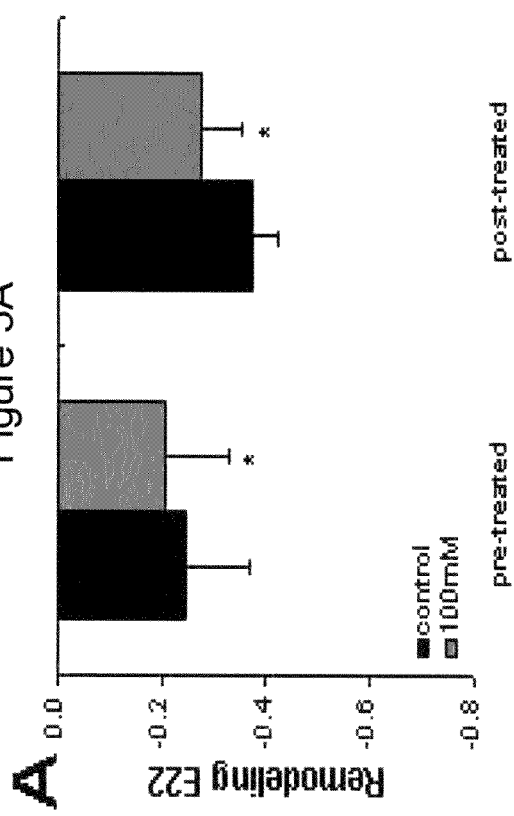
Figure 5C:
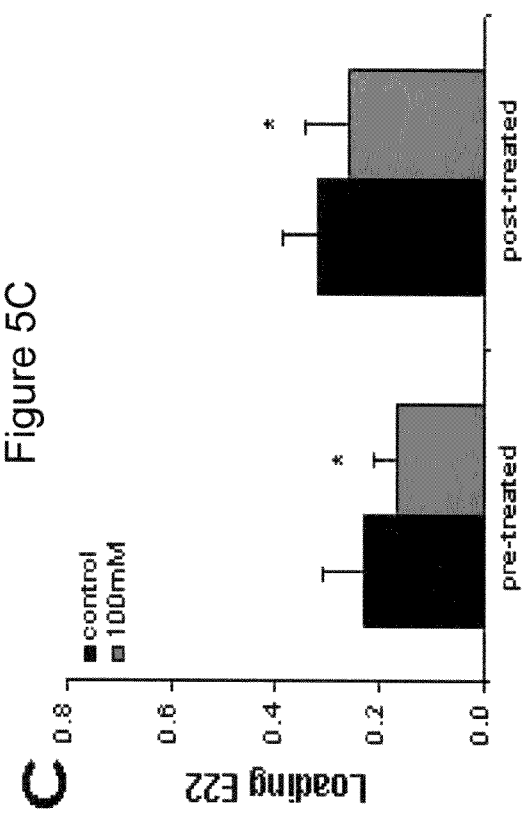

Biomechanical Stiffening Changes Induced in Collagenous Tissues by Cross-Linking by Nitrite The impact of sodium nitrite on vertical deformation of uniaxially constrained gels was measured during each phase of the experiment. FIG. 5(A) shows pretreatment at pH 4.0 for 24 hours with 100 mM sodium nitrite and posttreatment at pH 7.4 for seven days with 100 mM sodium nitrite both reduced vertical remodeling. *p<0.05 versus control. FIG. 5(B) shows pretreatment at pH 4.0 for 24 hours with 100 mM sodium nitrite and posttreatment at pH 7.4 for seven days with 100 mM sodium nitrite both reduced vertical deformation associated with preconditioning. FIG. 5(C) shows pretreatment at pH 4.0 for 24 hours and posttreatment at pH 7.4 for seven days with 100 mM sodium nitrite both reduced vertical deformation at 1 g equibiaxial load.

Example of Nitrite Concentration in Aqueous Humor of the Eye at pH 7.4

Figure 6:
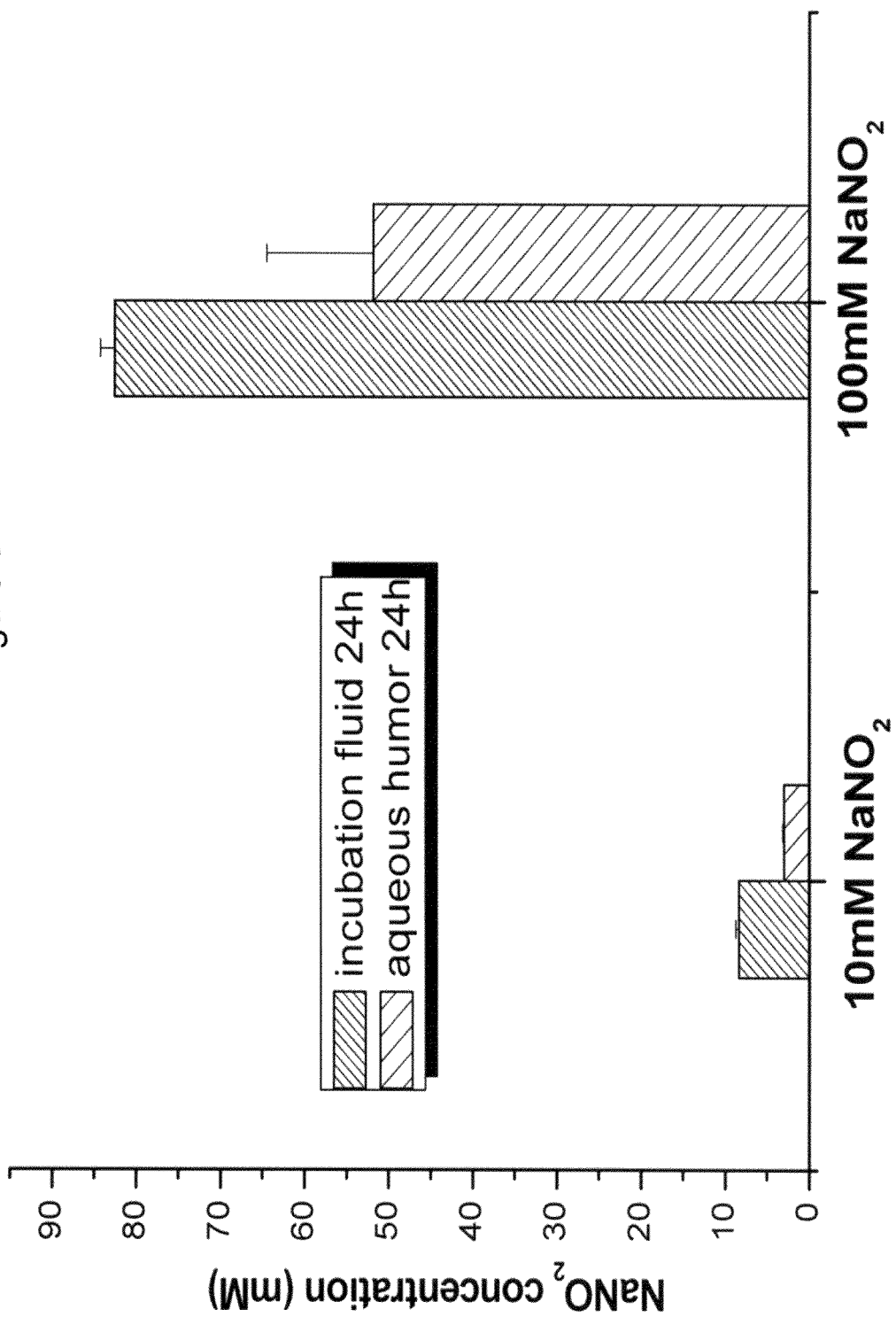
FIG. 6—Passage of nitrite into the anterior chamber at 24 hours, pH 7.4, and 4° C.

Adult porcine eyes were obtained within 12 hours of sacrifice and submerged in solutions of 0, 10, 100 mM $NaNO_2$ and 100 mM NaCl buffered with 50 mM $NaH_2PO_4/Na_2HPO_4$ (pH 7.4) following bubbling with 99% Argon/1% $O_2$ in order to limit the amount of potential nitrite auto-oxidation caused by oxygen. Penicillin/Streptomycin was added (10 µl/ml) to prevent bacterial overgrowth. After 24 hours of incubation at 4° C., the aqueous humor was sampled for nitrite concentration using a modification of the Greiss colorimetric assay. No nitrite was detected in either the buffer control or the 100 mM NaCl control. Nitrite concentration in the aqueous humor was 35.5% of the incubation fluid in the 10 mM $NaNO_2$ sample and 62.8% in the 100 mM $NaNO_2$ sample. These results suggest that there is a concentration dependent penetration of nitrite through the cornea as evidenced by FIG. 6.

Example of Nitrite Treated Eye Tissue at pH 5.0

Figure 7:
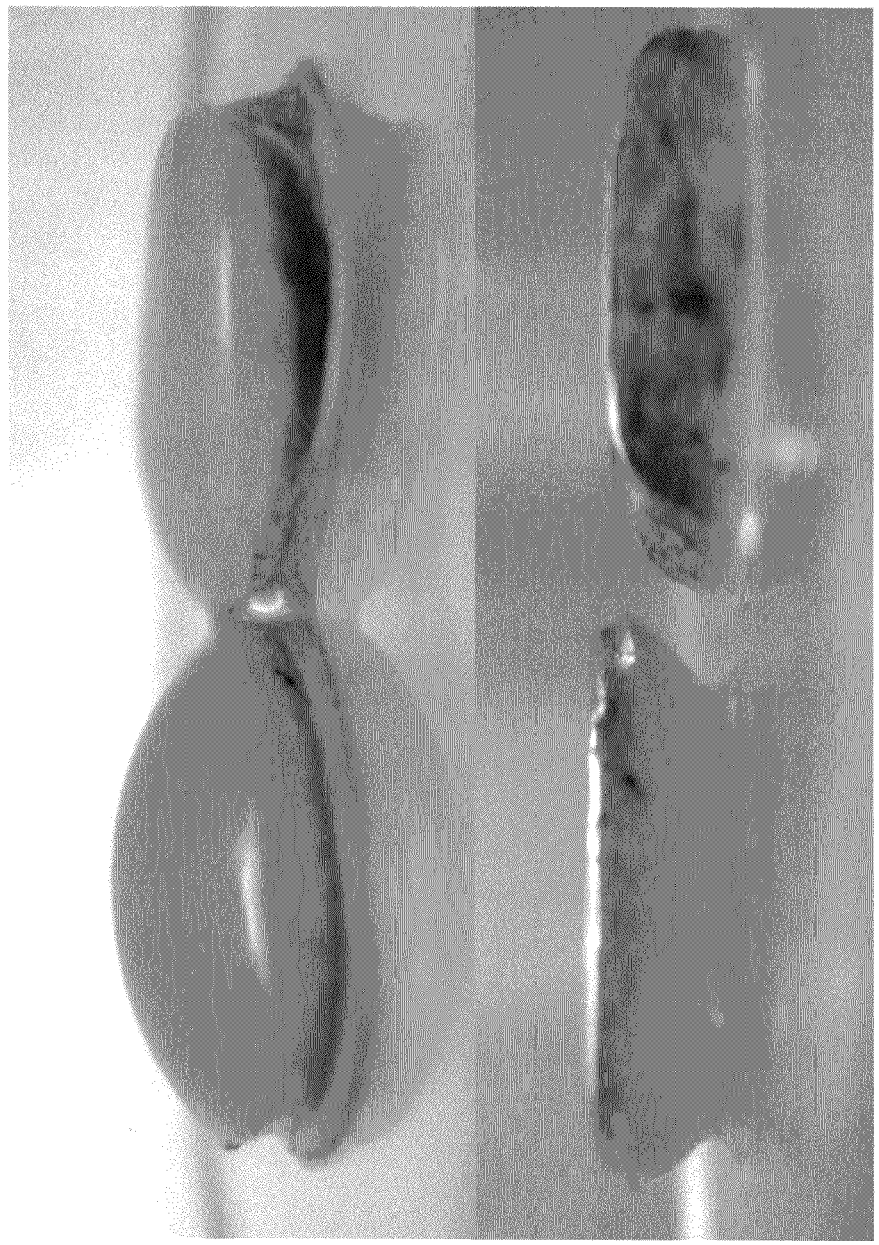
FIG. 7—Porcine cornea treated with 200 mM NaNO2, pH 5.0, 37° C., for 30 hours and untreated porcine cornea.
Figure 8:
FIG. 8—Porcine sclera treated with 200 mM NaNO2, pH 5.0, 37° C., for 30 hours and untreated porcine sclera.
Figure 9:
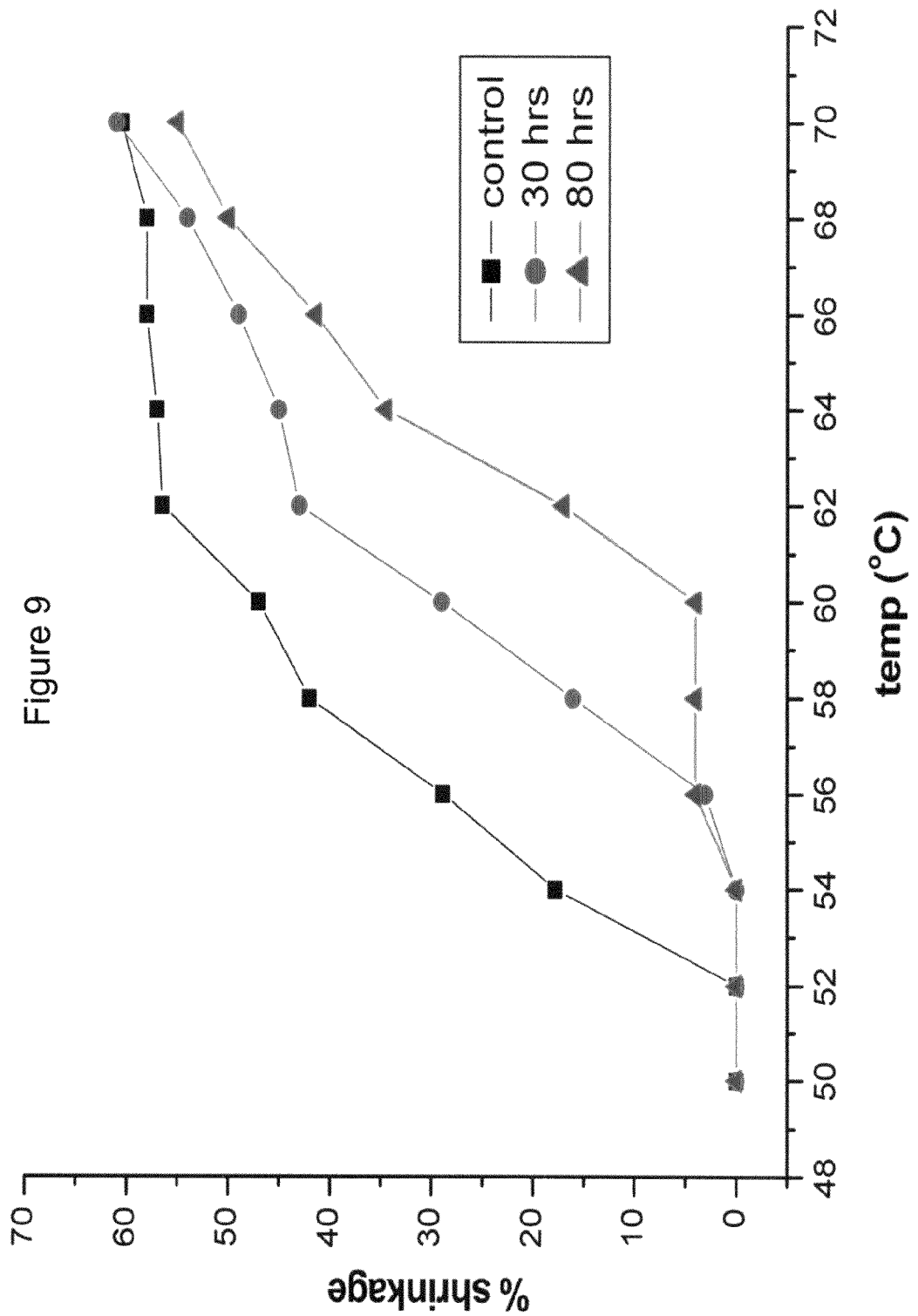
FIG. 9—Percent shrinkage of porcine cornea treated with 200 mM NaNO2, pH 5.0, 37° C., for 30 hours and 80 hours, and untreated porcine cornea, with 2° C. temperature increase every five minutes.

Adult porcine eyes were obtained within 12 hours of sacrifice and submerged in a solution of either 200 mM $NaNO_2$ or 200 mM NaCl buffered with 200 mM $NaH_2PO_4/Na_2HPO_4$ (pH 5.0). Penicillin/Streptomycin was added (10 µl/ml) to prevent bacterial overgrowth. After 30 hours of incubation at 37° C., the corneas were excised at the limbus and photographed. Dramatic contour changes in the corneas were observed in the samples cross-linked with $NaNO_2$ as compared with the NaCl control as demonstrated by FIG. 7. FIG. 8 demonstrates the dramatic contour changes are seen in sclera samples cross-linked with $NaNO_2$ as compared with the NaCl control.

After 30 and 80 hours of incubation at 37° C., the corneas were excised at the limbus and subjected to shrinkage temperature (thermal denaturation) analysis. The intact cornea was heated in 2° C. increments every 5 minutes using a digitally controlled water bath. The maximal dimensions in the long and short axis were measured using a micrometer under visualization with an operating microscope. The percentage of tissue shrinkage was then estimated by using 2 dimensional area calculations from the micrometer readings. The onset of tissue shrinkage was increased by approximately 4° C. following 30 hours of treatment and 8° C. following 80 hours of treatment as demonstrated in FIG. 8. These findings provide a general assessment of the degree of collagen cross-linking induced by reaction with nitrite.

Developments in Using β-Nitro Alcohol to Cross-Link Collagen

This study uses a combination of thermal denaturation temperature analysis, biomechanical testing, and cell culture cytotoxicity in a method development program aimed at identifying an effective and safe means of cross-linking collagenous tissues in vivo. These studies are followed by trials of topical cross-linking in the living rabbit eye. As a group, these are translational studies which are designed to lead directly to the initiation of a human clinical phase I trial.

Determining an Effective Way to Cross-Link the Cornea Using Nitro Technology under Conditions Simulating the Human Cornea (i.e., pH 7.4 and 34° C.)

Previous studies indicate that reactions with free nitrite ion under systemic physiologic conditions of neutral pH and body temperature induce collagen cross-linking (Paik, D. C., et al., 2001; Paik, D. C., et al., 2006). This has been shown through general measures of cross-linking such as increased thermal shrinkage temperature and increased resistance to enzymatic digestion, as well as more specific measures such as increased intermolecular covalent bonding (by SDS-PAGE) and the formation of lysine derived di- and tri-functional cross-links by LC/MS (unpublished). However, such reactions with free nitrite require high concentrations (i.e., 100-200 mM) and prolonged incubation periods (7-10 days). Thus, methods involving nitrite and related agents that significantly speed the reaction under conditions that simulate corneal tissue (pH 7.4 and 34° C.) have been developed.

Thermal shrinkage temperature or denaturation temperature ($T_s$) is a technique that has been used for decades in studying collagen cross-linking. As collagen fibers are progressively heated, a threshold temperature is reached at which point disruption of hydrogen bonding in the collagen molecule triple helix occurs, resulting in unwinding of the triple helices. The denaturation of tertiary protein structure results in a rapid shrinkage of the tissue of up to 80%. This phenomenon can be expressed in various ways including temperature of onset of tissue shrinkage, temperature at maximal tissue shrinkage, and temperature at 50% of maximal tissue shrinkage, for example. In addition, differential scanning calorimetry (DSC) is related to thermal shrinkage temperature analysis and is widely used to evaluate biomaterial cross-linking. Thermal shrinkage temperature is essentially a simplified version of DSC and can be used effectively to screen the cross-linking efficacy of compounds. For the purposes of this study, the onset of shrinkage is considered the $T_s$ and the temperature at which 50% of maximal shrinkage has occurred is $T_{50}$. Graphs depicting the relationship between degree of shrinkage and temperature indicate differences in degree of cross-linking between groups. Thus, stabilization of collagen fiber structures through non-enzymatic cross-linking increases $T_s$ and $T_{50}$. A 5° C. upward shift in $T_s$ for the anterior corneal stroma has been shown for the UVR cross-linking method (Spoerl, E., et al., 2004).

Polyethylene Box for Shrinkage Temperature Analysis

Figure 10:
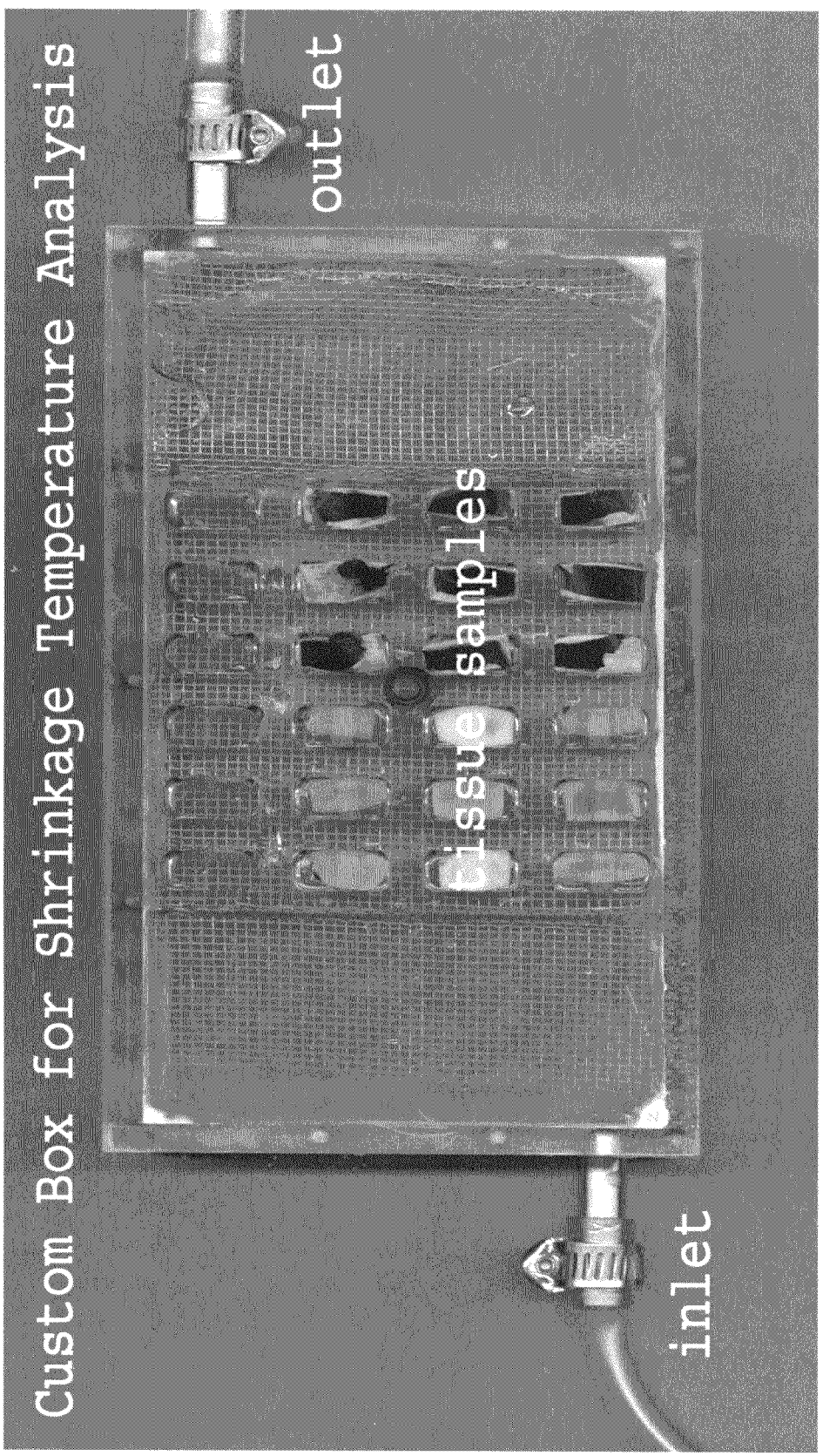
FIG. 10—Custom box for shrinkage temperature analysis, a general measure of collagen cross-linking.

A semi-automated system has been developed which increases the efficiency and accuracy of $T_s$ data collection. This system can perform multiple $T_s$ assays in succession, allowing rapid screening of a number of potential cross-linking agents and conditions. The setup consists of a custom built polyethylene box for shrinkage temperature analysis, as shown in FIG. 10, into which tissue samples are placed into an insert. Inlet and outlet fittings allow for constant circulation of heated water which is modulated by a digitally controlled water bath equipped with a water pump. The entire box is placed on a digital photo scanner connected to a Windows based computer. Beginning at 50° C. the temperature is raised at a rate of 1° C./min and serial scans are taken at every degree increase in temperature up to 80° C. Control pig corneas shrink at approximately 63° C. and cross-linked tissue at higher temperatures. As the tissue shrinks, the images are captured by the scanner. The image files are later analyzed for 2-dimensional area using NIH Image J software and % shrinkage calculations are made using Microsoft Excel for graphing purposes. This method obviates the need for removal of tissue pieces from the water bath with manual micrometer measurements as described by the UVR group (Spoerl, E., et al., 2004). Thus, the labor involved in acquiring data is lessened and the accuracy using image analysis is improved.

Figure 11:
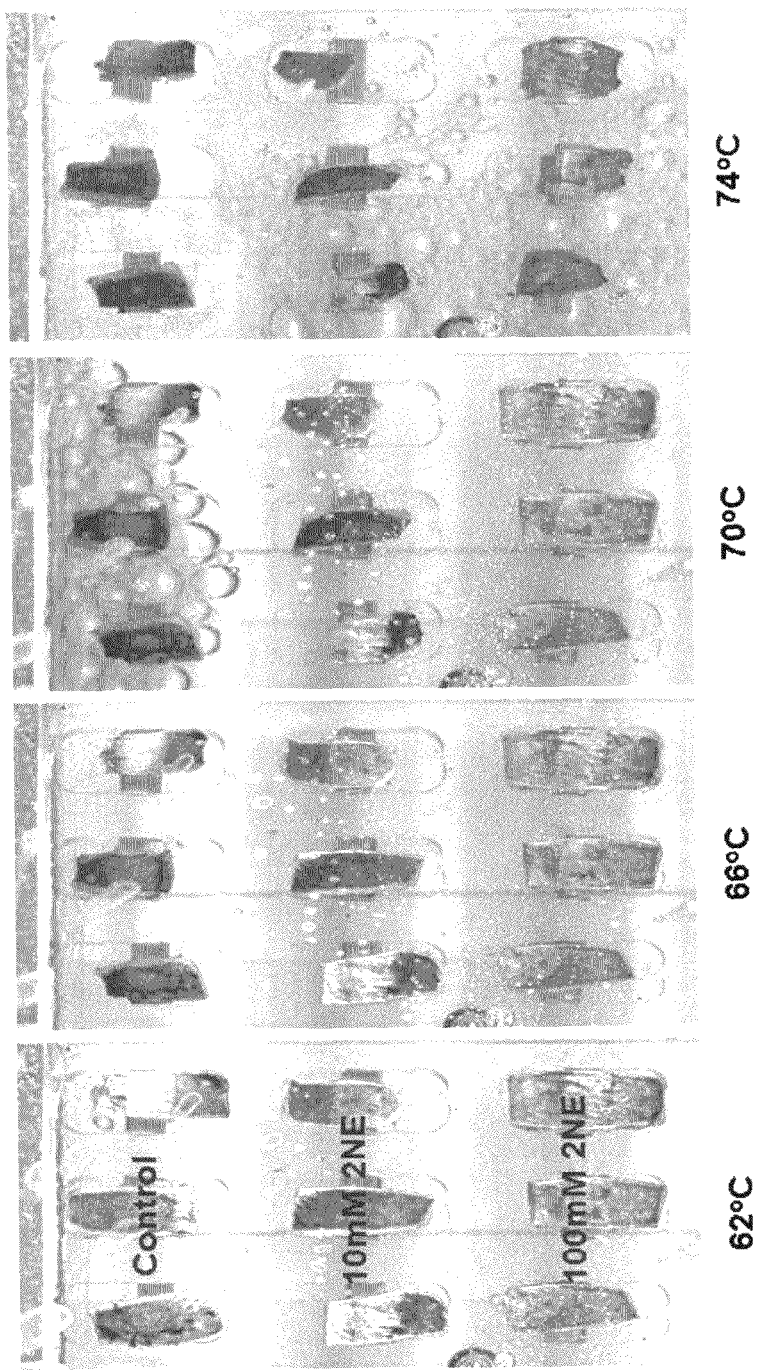
FIG. 11—Example of shrinkage temperature changes in cross-linked porcine sclera.

FIG. 11 illustrates an example of shrinkage temperature change in porcine sclera cross-linked with 2-nitroethanol (2NE). Serial images are shown depicting shrinkage of control samples in the 66° C. image but not the 2-nitroethanol. At a higher temperature (i.e. 70° C.), the 10 mM 2-nitroethanol samples shrink. Finally, at the highest temperature (i.e. 74° C.), all the samples have shrunken, including the 100 mM 2-nitroethanol samples. This example depicts the concept that cross-linked collagenous tissues require higher temperatures in order to shrink (or denature).

Using this simple, reproducible assay enables the screening of a number of compounds for cross-linking efficacy. This is first performed using porcine eyes because of their low cost. Follow up studies can be performed using human eyes. Porcine eyes are obtained within 6 hrs of sacrifice (Hatfield Meat Packing, Inc., Hatfield Pa.). Eyes showing clear corneas and intact epithelia are chosen for study. 10×4 mm strips are obtained from the central corneal region along the superior-inferior axis (2 per eye). Each strip is then cross-linked using a nitro agent. The incubation solution is 20% Dextran (T500) [to prevent tissue swelling] in 0.2 M $NaH_2PO_4/Na_2HPO_4$ (pH 7.4) with various concentrations of nitro agent (i.e. 1, 10, and 100 mM). At these concentrations pH is well maintained over the course of 96 hrs. The samples are then placed in 2 mL microcentrifuge tubes with 1 mL of incubation solution and reacted in a 34° C. water bath (simulating corneal temperature—Girardin, F., et al., "Relationship between corneal temperature and finger temperature," *Arch. Opthalmol.* 1999; 117:166-169) for 24-96 hrs. Following incubation, the samples are evaluated for degree of cross-linking using the $T_s$ assay as described above.

From the data, $T_s$ curves are generated for each compound and condition studied. Each data point is the average of 3 independent samples. Differences between groups can be compared for statistical significance using simple t-test analyses comparing $T_s$ and $T_{50}$. Using these curves, comparisons are made between compounds regarding their cross-linking efficacy. The targeted change for onset of shrinkage temperature is 5° C. This is the level of change reported by the UVR group for cross-linking. Compounds are sought that can produce the target $T_s$ (−5° C.) shift at the lowest concentration and shortest possible incubation times. Ultimately, however, the choice of compound (or compounds) for cross-linking in the living eye is determined based not only on its cross-linking efficacy but also its cytotoxicity, which is determined as described herein.

Comparing β-Nitro Alcohols

Different β-nitro alcohols are compared with regard to cross-linking efficacy. At least 3 of the lower order β-nitro alcohols related to 2-nitroethanol (i.e. 2-nitro-propanol, 2-nitro-1-pentanol), which is effective as a cross-linking compound, are studied. This determines the differences in cross-linking efficacy between various β-nitro alcohols. It also provides potential alternatives for in vivo rabbit eye cross-linking in the event that any of these compounds exhibit significant cytotoxicity to corneal cells. When a candidate agent is identified (such as 2-nitroethanol) human eye bank corneas are tested in order to confirm the effects in human tissue. Because these compounds are used for cross-linking living corneas over the course of weeks, cross-linking efficacy occurring over many days at low concentrations are studied. This simulates the in vivo use of serial reagent application lasting on the order of weeks. For example, if 1 mM is the highest non-toxic level for 2-nitroethanol, a time course study is conducted in which tissue samples are reacted over the course of 2-3 weeks by replacing the incubation fluid daily with 1 mM 2-nitroethanol. The goal in this regard is to determine the length of duration necessary for adequate cross-linking at the non-toxic dose level.

Previous studies using acidified $NaNO_2$ indicate that cross-linking is enhanced by lowering the pH. This indicates that nitrous acid and the subsequent formation of nitrosating species such as nitrosonium (+NO) and/or dinitrogen trioxide ($N_2O_3$) are involved in cross-linking. If this were the case, it would not be predicted that the β-nitro alcohols could cross-link as well. However, 2-nitroethanol does induce cross-linking. Nitrous acid (i.e. $NaNO_2$ compared at pH 3, 5, and 7.4), isopentyl nitrite (a well known nitrosating agent—Williams, D. L. H., "Reagents effecting nitrosation. In: Nitrosation Reactions and the Chemistry of Nitric Oxide," 2004, ed., Elsevier, Chapter 1:1-34; Iglesias, E. and Casado, J., "Mechanisms of hydrolysis and nitrosation reactions of alkyl nitrite in various media," *Int. Rev. Phys. Chem.* 2002; 21(1):37-74), and 2 selected diazeniumdiolate compounds, dipropylenetriamine NONOate (DPTA/NO) (t/2=3 hr) and diethylenetriaamine NONOate (DETA/NO) (t/2=20 hr) (Kong, L., et al., "Deamidation of peptides in aerobic nitric oxide solution by a nitrosative pathway," Nitric Oxide 2006; 14(2):144-151) are used. By using 4 distinct means for producing nitrosation, it can be determined if nitrosation induces collagen cross-linking (as determined by a shift in $T_s$). Incubations are performed at 100 mM concentrations. Confirming or rejecting nitrosation as a cross-linking mechanism provides important information. It is well known that nitrosation of a primary amine forms an unstable diazo compound which undergoes dediazoniation ($N_2$ gas is liberated). In this way nitrosation of the primary ε-amines groups in lysine and hydroxylysine (important cross-linking sites in collagen) with resultant deamination is a plausible mechanism.

Finally, there are several potential benefits to using free nitrite as a topical stiffening agent. First, nitrite is a physiologic molecule and is well tolerated by cells. Second, based on preliminary studies nitrite appears to penetrate the corneal epithelium. This being said, at neutral pH, the reaction with nitrite is rather slow, requiring several days for cross-linking effects to occur. Thus, whether the rate of reaction with free nitrite at neutral pH can be increased through use of a catalyst is studied. Previous studies by Keefer, et al. in the early 1970's showed that neutral pH nitrite reactions could be enhanced by the addition of aldehyde catalysts. Keefer, L. K. and Roller, P. P., "N-nitrosation by nitrite ion in neutral basic medium," *Science* 1973; 181(4106):1245-1247. Such compounds included pyridoxal (vitamin B6) which should be well tolerated by cells and other aldehyde compounds, which can be added to the nitrite solution in low concentrations in order to speed the reactions.

Testing that Corneal Cross-Linking through Nitro Technology Increases Biomechanical Stiffness Properties Commensurate with UV/Riboflavin Therapy It has been shown that the keratoconic cornea displays alterations in elasticity compared to normal corneas, indicating a decreased stiffness. Andreassen, T. T., et al., 1980; Nash, I. S., et al., "Comparison of mechanical properties of keratoconus and normal corneas," *Exp. Eye Res.* 1982; 35:413-423; Edmund, C., "Corneal elasticity and ocular rigidity in normal and keratoconic eyes," *Acta Opthalmol.* 1988; 66:134-140. Thus, the ultimate goal of corneal cross-linking is to provide mechanical stabilization to the cornea by increasing the tissue stiffness. Although $T_s$ measurements provide a reasonable assessment of the degree of tissue cross-linking, it is necessary to establish the degree of biomechanical strength imparted by nitro technology through mechanical testing. Thus, the range of biomechanical stiffness achievable through these reactions is established.

Figure 12:
FIG. 12—Planar biaxial material testing system with sample loaded in center.

Fresh porcine and human cadaver whole corneas are cross-linked using methods developed in the first part of Determining an Effective Way to Cross-Link the Cornea Using Nitro Technology under Conditions Simulating the Human Corea (i.e., pH 7.4 and 34° C.). Based on preliminary studies, this is a β-nitro alcohol compound similar or identical to 2-nitroethanol. However, this can also include nitrosating compounds such as the diazeniumdiolates if they are determined to be effective cross-linkers as well as free nitrite with a catalyst. All corneas are tested while fully immersed in hypertonic 30% NaCl (to prevent swelling) with phosphate buffer (~pH 7.4) at room temperature. By using 30% NaCl it has been determined that after 4 hours tissue thickness increases by less than 10%. Using lower concentrations of NaCl results in thickness increases greater than 10% and therefore is not suitable for mechanical testing. Dissected corneas are attached to a custom biaxial stretching device, shown in FIG. 12, using two metallic hooks per side. Graphite markers are placed on the center of the anterior surface with adhesive and imaged for optical deformation tracking with a charged coupled device (CCD) video camera mounted above the specimen. Each specimen is subjected to three loading protocols: uniaxial stretches in the horizontal (i.e. naso-temporal) and vertical (superior-inferior) directions, and equibiaxial stretch. Each test is performed from a 5 g preloaded equibiaxial state for 10 cycles, 20 seconds per cycle. Equibiaxial tests are repeated throughout the test to verify the repeatability of the mechanical response. Grashow, J. S., et al., "Biaxial stress-stretch behavior of the mitral valve anterior leaflet at physiological strain rates," *Ann. Biomed. Eng.* 2006 February; 34(2):315-325.

During testing, custom software acquires data simultaneously from the CCD video camera (for marker tracking) and the force transducers, allowing calculation of stress-strain curves for each test. During the last loading cycle (i.e. #10), the deformation of the markers is used to calculate the deformation gradient F and the Green strain tensor, $E=0.5(F^T*F-I)$, where I is the identity tensor. Specimen thickness is calculated prior to testing in the unloaded state by averaging at least five measurements taken at different locations of the cornea using a caliper. The length of each side of the cornea (i.e., length between sutures) is measured from images taken from the bottom of the sample. The cross-sectional reference area of the sample is calculated and the first Piola-Kirchoff stresses P are obtained by dividing the measured forces by the reference area in the appropriate direction. Assuming incompressibility (J=det F=1) and plane stress ($F_{13}$, $F_{23}$, $F_{31}$, and $F_{32}$ are equal to zero), Cauchy stresses t are computed for the horizontal ($t_{11}$) and vertical ($t_{22}$) directions. No less than 3 samples are studied for each treatment group. Since the cornea is an anisotropic tissue (Dupps, W. J. and Wilson, S. E., "Biomechanics and wound healing in the cornea," *Exp. Eye Res.* 2006; 83:709-720), using the biaxial tester rather than a uniaxial device provides the advantage of obtaining stress-strain relationships along both the superior-inferior as well as the nasal-temporal axis. The methods developed and range of stiffness changes determined are used to predict the changes that are inducible in the living rabbit eye. It is also allows comparisons to be drawn with the UVR published values for biomechanical stiffness changes induced by UVR and other chemical cross-linking agents. Wollensak, G. and Spoerl, E., "Collagen crosslinking of human and porcine sclera," *J. Cataract Refract. Surg.* 2004; 30:689-695.

Testing that Corneal Cross-Linking through Nitro Technology is Tolerated by Corneal Cells A number of aldehyde cross-linking agents have been used previously for in vitro collagen cross-linking. Although effective cross-linking agents, their in vivo utility is limited by their significant cytotoxicity. The clinical utility of this nitro technology is determined both by its efficacy as a cross-linking agent as well as its level of cytotoxicity. Therefore, relevant cytotoxic effects using compounds determined to be efficient cross-linking agents were examined and include nitrite and related compounds. The cytotoxic effects on corneal endothelial cells, keratocytes, and epithelial cells were examined. Of these, the effects on endothelial cells are the most important, since these cells are principally responsible for maintaining corneal transparency through regulation of stromal water balance and lack the ability to regenerate in vivo.

Primary cultures of bovine corneal endothelial cells, keratocytes, and epithelial cells are grown in vitro. For endothelial cells, fresh bovine eyes were obtained. The entire corneal ring was cut out and placed into a concave container used for the storage of contact lenses. A 0.05% trypsin-0.02% EDTA solution was applied onto the endothelium for 5 min in order to dissociate the cells. After 5 min of digestion, the endothelial cells were mobilized using a glass spatula. Finally, the solution containing suspended endothelial cells was pipetted and transferred to a 25 $cm^2$ cell culture flask filled with 20 ml DMEM containing 10% fetal calf serum which quenches the digestive activity of trypsin. The primary cultures were then placed in a cell culture oven at 37° C. and gassed with 6% carbon dioxide. Cell growth was evaluated every other day using an inverted phase contrast microscope (Zeiss Axiovert L5). The media was changed every 3-4 days. Confluence with about $2.5 \times 10^6$ cells per flask is reached after 2-3 weeks. For passaging, the confluent stock cultures were dissociated and detached using a 0.05% trypsin-0.02% EDTA solution. The free floating cells were centrifuged at 230 g, again transferred to culture flasks and suspended in the cell culture medium. Passaging is performed every $2^{nd}$ week at a split ratio of 1:3. Grant, M. B., et al., "Effects of epidermal growth factor, fibroblast growth factor, and transforming growth factor-β on corneal cell chemotaxis," *Investigative Opthalmology & Visual Science* 1992; 33(12):3292-3301; Orwin, E. J. and Hubel, A., "In vitro culture characteristics of corneal epithelial, endothelial, and keratocyte cells in a native collagen matrix," *Tissue Engineering* 2000; 6(4):307-319; Bednarz, J., et al., "Effect of three different media on serum free culture of donor corneas and isolated human corneal endothelial cells," *Br. J. Opthalmol.* 2001; 85:1416-1420. The approach for preparing primary keratocyte cultures is similar to that described for endothelial cells, with the exception being that keratocyte are grown from explanted tissues as described by Wollensak, G., et al., "Keratocyte apoptosis after corneal collagen cross-linking using riboflavin/UVA treatment," *Cornea* 2004; 23(1):43-49. Similarly, the protocol for growing epithelial cells is straightforward and has been described in detail. This includes the use of a specialized growth medium for corneal epithelial cells. Grant, M. B., et al., 1992, Orwin, E. J. and Hubel, A., 2000. After growing in 96-well plates and with cells at 80-90% confluence, compounds of interest were added into the culture medium at a range of concentrations (0.001-1%). Following a 48 hrs incubation period, a cell suspension was obtained by trypsinization and dead cells were stained using 0.4% trypan blue for 5 min. The live/dead cells were then counted using a hemocytometer and the dead cell percent calculated. Three wells were used for each condition. Based on preliminary experiments with 2-nitroethanol, a toxicity threshold occurs (>1 mM) such that below the threshold all cells are alive and above the threshold all cells are dead. A similar protocol was performed to evaluate the degree of apoptosis and necrosis, this utilizes annexin V and propidium iodide staining according to the manufacturer's protocol (Molecular Probes, Inc.).

An abrupt toxicity threshold was observed as was described by the UVR group, a table was generated for each compound of interest, indicating the concentrations below and above the threshold as either being non-toxic (i.e. minus sign −) or toxic (plus sign +)(Tables 1 and 2). Trypan blue and PI staining provide a general indication of cytotoxicity and annexin V staining can detect apoptosis. However, clearly there are more subtle alterations in cell function that may be pertinent to cytotoxicity. For example, alterations in gene expression and potential mutagenicity could be occurring at a level below the threshold for necrosis. These more subtle aspects are reserved for later phases of drug development during which time extensive evaluation by high throughput technology can be conducted. Several toxicity/mutagenicity studies have already been published. For instance, β-nitro alcohols are known to have a very low mutagenicity (Conaway, C. C., et al., 1991) and animal toxicity profiles (Jung, Y. S., et al., 2004). As such, they have been proposed for use in animal feeds in order to control food borne pathogens in ruminants and chickens where they exhibit bacteriostatic activity (Horrocks, S. M., et al., 2007).

TABLE 1

Cytotoxic threshold (using trypan blue) of primary bovine corneal endothelial cells following 48 hrs exposure

| (mM) Concentration | 2-nitroethanol | 2-nitro-1-propanol | 3-nitro-2-pentanol |
|---|---|---|---|
| 10 | + | + | + |
| 7 | + | + | + |
| 5 | + | + | + |
| 3 | + | + | + |
| 2 | − | + | − |
| 1 | − | + | − |
| 0.75 | − | − | − |
| 0.5 | − | − | − |
| 0.1 | − | − | − |

+ = positive trypan blue staining = cells dead
− = no trypan blue staining = cells alive

TABLE 2

Apoptosis (Annexin V) staining of bovine corneal
endothelial cells following a 48 hrs exposure

| (mM) Concentration | 2-nitroethanol | 2-nitro-1-propanol | 3-nitro-2-pentanol |
|---|---|---|---|
| 3 | + | + | + |
| 2 | − | + | − |
| 1 | − | + | − |
| 0.75 | − | − | − |
| 0.5 | − | − | − |
| 0.1 | − | − | − |

+ = positive trypan blue staining = cells dead
− = no trypan blue staining = cells alive As demonstrated herein, the highest tolerated level for 2-nitroethanol on ARPE-19 cells is 1 mM. At this concentration, $T_s$ for porcine cornea was shifted 1-2° C. when serially applied over 6 days and $T_s$ for porcine sclera was shifted 2-3° C. when serially applied over 10 days. Based on these studies, it is believed that serial application using lower doses can produce cross-linking effects similar to those induced at higher concentrations for shorter incubation periods. This therapy may produce corneal cross-linking over a relatively long period (2-8 weeks) using a dose of drops that would produce a subtoxic stromal tissue level.

TABLE 3

The cytotoxic threshold compares favorably with
other ophthalmic agents

| Compound | Toxic concentration | Time of exposure | Species of origin (corneal endothelial cell) | Assay method | citation |
|---|---|---|---|---|---|
| 2-nitroethanol | 3 mM (0.0273%) | 48 hrs | Bovine primary | Trypan blue | |
| 2-nitro-1-propanol | 1 mM (0.0105%) | 48 hrs | Bovine primary | Trypan blue | |
| 3-nitro-2-pentanol | 3 mM (0.0339%) | 48 hrs | Bovine primary | Trypan blue | |
| Ciprofloxacin | 3.02 μM (0.0001%) | 15 min | Human | Calcein AM | Skelnik 2003 |
| Moxifloxacin | 2.49 μM (0.0001%) | 15 min | Human | Calcein AM | Skelnik 2003 |
| Gatifloxacin | 2.66 μM (0.0001%) | 15 min | Human | Calcein AM | Skelnik 2003 |
| Levofloxacin | 2.69 μM (0.0001%) | 1 hr | Human | Calcein AM | Skelnik 2003 |
| Benzalkonium chloride | (0.0001%) | 3 hrs | Rabbit organ culture | Electron microscopy | Green 1977 |
| Cetylpyridinium chloride | 10 μM | 3 hrs | Rabbit organ culture | Electron microscopy | Green 1977 |
| Daunorubicin | 948 nM (0.00005%) | 7 days | Human immortalized | Calcein AM | Garweg 2006 |
| Mitomycin C | 299 nM (0.00001%) | 7 days | Human immortalized | Calcein AM | Garweg 2006 |
| Azathioprine | 220 μM (0.005%) | 7 days | Human immortalized | Calcein AM | Garweg 2006 |
| Cyclosporin A | 41 μM (0.005%) | 7 days | Human immortalized | Calcein AM | Garweg 2006 |
| Providone iodine | (0.1%) in serum free medium | 12 hrs | Bovine primary | Trypan blue | Naor 2001 |

Testing that Corneal Cross-Linking through Nitro Technology Has Efficacy and is Safe for the Living Eye Evaluation of the efficacy and safety in the living eye is a crucial prerequisite leading to a phase I human clinical trial. The testing described above provides the necessary background information for use of this technology in the living eye. Compound selection, concentration, duration of exposure, toxicity thresholds, and target biomechanical effects are all pre-estimated from the biochemical, biomechanical, and cell biology studies described above. This provides a general range of the conditions necessary for cross-linking the living rabbit cornea. However, considerations with living eyes are far different from in vitro studies. As such, much of the experimental protocol particularly concerning dosing is determined empirically. The results establish the in vivo efficacy and safety of this technology and dictate the feasibility of a human phase I clinical trial.

A total of 20 young female New Zealand white rabbits weighing 2.0 to 2.5 kg are obtained and maintained in the CUMC animal facility on the $8^{th}$ floor of the Harkness Eye Institute. After a 1 week acclimatization period, a pre-treatment baseline evaluation is performed using 2 sophisticated, widely used, non-invasive instruments. One of these is the Ocular Response Analyzer (ORA) from Reichert, Inc., which is used to measure intraocular pressure (IOP) and biomechanical properties such as corneal hysteresis (CH) and corneal resistance factor (CRF). Pepose, J. S., et al., "Changes in corneal biomechanics and intraocular pressure following LASIK using static, dynamic, and noncontact tonometry," *Am. J. Opthalmol.* 2007; 143:39-47. The other instrument is the ConfoScan4 from Nidek Corp., which is a fully digital ophthalmic confocal microscope system. This is used to evaluate corneal thickness (pachymetry, an index of endothelial cell function) and cell toxicity through evaluation of corneal endothelial cells, keratocytes, and epithelial cells. The advantage of using the ConfoScan4 is that the system is fully automated for cell counts and includes important parameters of endothelial cell health. This includes measurements of mean cell density, mean cell area, coefficient of variation in cell size (polymegathism), and the percentage of hexagonal cell (pleomorphism). Bourne, W. M. and McLaren, J. W., "Clinical responses of the corneal endothelium," *Exp. Eye Res.* 2004; 78:561-572. In addition, corneal thickness and percentage of viable keratocytes and epithelial cells are obtained during the same examination.

During each evaluation, the animals are sedated using an intramuscular injection of ketamine hydrochloride 10% (35 mg/kg) and xylazine hydrochloride (5 mg/kg) which is dosed on a by-weight basis. All measurements are obtained with the animals under anesthesia. After acquisition of the baseline values of each animal using the ORA and ConfoScan4, the treatment process begins. Instillation of the topical cross-linking solution to the right eye with the left eye as a control is performed daily for a 2-8 week period. Non-invasive measurements are taken weekly. Of note, when the drops are applied, the compound is rapidly mixed with the tear film and most of the administered drop is lost to drainage in the first 15-30 seconds. Since the tear turnover rate is approximately 16% per minute, most of the compound is expected to disappear within 10 minutes. Thus, the concentration rapidly declines to a fraction of the applied dose and the amount of time that the epithelium is exposed to the agent is on the order of seconds. McGee, D. H., et al., "Safety of Moxifloxacin as shown in animal and in vitro studies," *Survey of Opthalmology* 2005; 50(suppl. 1):S46-S54. The ability of the compound to enter the corneal stroma is an important consideration. Preliminary studies indicate that free nitrite is able to pass into the stroma and into the aqueous chamber with a concentration dependent effect. However, these studies were performed on cadaver eyeballs over 24 hrs. Thus, it is not possible to positively predict, based on those experiments, what the permeability is in a living rabbit eye. Since compounds such as nitrite and 2-nitroethanol are hydrophilic, they are not expected to be able to pass through the lipid bilayer of cell membranes by passive diffusion. However, there are several transporters present in the corneal epithelium that could potentially allow rapid passage of these types of compounds into the stroma. Transporters for various amino acids and compounds such as taurine could provide a means for easy entry. Mannermaa, E., et al., "Drug transport in the corneal epithelium and blood-retina barrier: emerging role of transporters in ocular pharmacokinetics," *Advanced Drug Delivery* 2006; 58:1136-1163.

Initial studies indicate that a 1 mM concentration of 2-nitroethanol can cross-link corneal tissue and is tolerated by living epithelial cells. In vitro findings are extrapolated to considerations related to the living eye.

An eye drop concentration for testing live rabbit cornea, to achieve local stromal concentration of 1 mM 2-nitroethanol, is determined largely on an empirical basis to penetrate through the corneal epithelium. However, nitrite is known to possess the ability to bind non-covalently with tissue and can accumulate differentially in tissues. Bryan, N. S., et al., "Cellular targets and mechanisms of nitros(yl)ation: an insight into their nature and kinetics in vivo," *PNAS* 2004; 101(12): 4308-4313. Non-covalent binding is also evidenced by the in vitro finding that following reactions with nitrite and collagen, complete removal of free nitrite requires extensive dialysis using high concentration buffers and/or use of detergents such as SDS and guanidine. Thus, introducing the agents into the stroma may allow for accumulation of reagent locally.

Experiments are conducted using a relatively high dose of agent (i.e. 100 mM or 1%) on only 2 rabbits. This is applied through continuous application of drops for 5 minutes applied daily. By following the cytotoxic effects using the ConfoScan4 and biomechanical properties using the ORA the drug dosage and duration of exposure is able to be adjusted to compensate for changes in the cytotoxicity and/or biomechanics. Whether the corneal cells can tolerate the application of a 100 mM 2-nitroethanol solution applied daily is determined. The duration of application in these experiments is guided by evaluation of cell viability. If a negative change is observed in endothelial cell parameters, for example, the concentration or length of continuous drop application (i.e. 5 min) is decreased. Dosage modulations in the initial experiments are performed on a per weekly basis and are dictated by data obtained from the ConfoScan4. A cytotoxic change is indicated by a decrease in mean cell density and/or mean cell area as well as by an increase in pleomorphism or polymegathism. The threshold for changing dosing is a 10% or greater negative change in any of the 4 endothelial cell parameters. Simultaneously, data obtained by the ORA during the same treatment process provides a real time assessment of stiffness change that is coupled with cell toxicity parameter from the ConfoScan4. Thus, even prior to obtaining post-mortem biomechanical stiffness data, some inference is made as to whether the treatment results in corneal stiffening. After the total treatment period is complete (i.e. 2-8 weeks), the animals are sacrificed by $CO_2$ narcosis and the eyes removed for post-mortem mechanical testing. That is, whole excised corneas are mounted in the biaxial material tester and stress-strain curves generated in order to draw comparisons to the ORA stiffness data as well as published data related to the UVR cross-linking method.

Following this initial experiment, subsequent experiments are performed based on the observed efficacy and cytotoxicity observed at the initial dosage and duration trial with 2 rabbits. The treatment regimen can then be modulated either to increase or decrease the concentration of agent, time of continuous application (i.e. minutes), and duration of treatment (i.e. weeks) to optimize the cross-linking efficacy and minimize the toxicity. Ultimately, up to 6 groups of 3 rabbits per group (i.e. 3 rabbits at a time) for a total of 18 rabbits are used. Using 6 different groups allows testing of at least 2 separate agents with at least 3 different dosing regimens. In general, higher concentrations are used for shorter durations and lower concentrations for longer durations. Thus, for each group weekly time points with measurements of corneal thickness, endothelial cell parameters, keratocyte counts, and epithelial cell counts from the ConfoScan4 are available; and corneal thickness, IOP, corneal hysteresis, and corneal resistance factor from the ORA. This generates data in table form.

Most of the other aspects of this application involve simple comparisons of group means which are analyzed statistically using simple t-tests. In this live rabbit study, the interest is in testing the null hypothesis of no treatment effect (the profiles of means [for y] are parallel in the treatment group and the control group and also at the same level). The primary analysis method to be used is multivariate linear regression that separately models the means and the covariance structure. This is necessary to estimate correct tests of hypotheses and confidence intervals since the measurements are not independent (repeated measures within rabbits) of each other. The statistical program SAS "Proc mixed" are used to perform the analysis. An example program for this analysis is shown below:

[Proc mixed data=\*\*\*; Class id trt week t; Model y=trt week trt\*week/s chisq; Repeated t/type=cs subject=id r;]

The main predictor is treatments (trt). The association of treatment effect and change in y is evaluated by the treatment*week interaction. Compound symmetry (CS) covariance structure is used if the covariance structure matches the data obtained. If CS covariance structure does not match the data obtained, the best fitting model using maximum likelihood tests for nested models and Akaike's information Criteria (AIC) for non-nested models is selected. Covariates are not necessary since both treated and control data is nested in the same animal (i.e. left eye control, right eye treated). Similar analytic strategies are used for other measurements b, c, d, . . . (i.e. thickness, IOP, etc.).

The nitro agent may be able to cross-link cornea in vitro and produce biomechanical stiffness yet be unable to produce the same effects in a living eye. In this case, the agent may exhibit poor penetration through the corneal epithelium resulting in low or absent levels of agent in the stroma. In addition to the strategies outlined above, one alternative is to create a window or grid lines through the epithelium to allow passage of the compound into the stroma (this technique is used with UVR therapy). In this case the cornea is saturated by continuous application with the epithelium removed and thereby achieve high stromal tissue concentrations. Since epithelial regeneration requires 3-4 days, the agent is applied daily or on an increased dosage schedule (i.e. three times per day or more) until the epithelium has reformed.

The agent may be able to cross-link cornea in vitro and produce biomechanical stiffness yet be unable to produce the same effects in a living eye. The nitro agent can be photolyzed to increase effectiveness. As with riboflavin, nitrite ($\lambda_{max}$=350 nm) and other nitro compounds undergo well-known photochemical reactions. Fischer, M. and Warneck, P., "Photodecomposition of nitrite and undissociated nitrous acid in aqueous solution," J. Phys. Chem. 1996; 100:18749-18756. Iontophoresis and the use of collagen shields are used to increase agent effectiveness. The first methods require the use of an electrical charge device which is used to aid the passage of cross-linking compounds across the corneal epithelium and has been used to deliver antibiotics into the corneal stroma. Frucht-Pery, J., et al., "A. Iontophoresis-gentamicin delivery into the rabbit cornea, using a hydrogel delivery probe," Exp. Eye Res. 2004; 78:745-749. The second technique involves saturating a collagen shield with cross-linking agent and applying it to the cornea. Friedberg, M. L., et al., "Collagen shields, iontophoresis, and pumps," Opthalmology 1991; 98:725-732. Prolonged release from the shield could then occur over the course of several days.

Results

Efforts regarding the concept of nitrite induced collagen cross-linking have been directed at elucidating age-related damage mechanisms in human disease. Indeed, age-related non-enzymatic collagen cross-linking is a well-known phenomenon occurring in numerous organ systems. Since human nitrite exposure can occur from various important sources such as smoking, inflammation, and diet, the finding that nitrite induced collagen cross-linking mimics aging changes has led to the hypothesis that age-related tissue damage may result from lifetime nitrite exposures. The initial studies have documented increases in resistance to enzymatic digestion (Paik, D. C., et al., "The nitrite/collagen reaction: non-enzymatic nitration as a model system for age-related damage," Con. Tis. Res. 2001; 42(2):111-122), as well as increased collagen primary chain covalent cross-linking by SDS-PAGE (Paik, D. C., et al., "Nitrite induced cross-linking alters remodeling and mechanical properties of collagenous engineered tissues," Con. Tis. Res. 2006; 47:163-176). It has been discovered that fibroblast-populated type I collagen gels show an increase in tissue stiffening following nitrite cross-linking. Although the conclusions drawn from these studies implicate nitrite cross-linking as an age-related deleterious process, the collagen cross-linking can have therapeutic applications.

Figure 3:
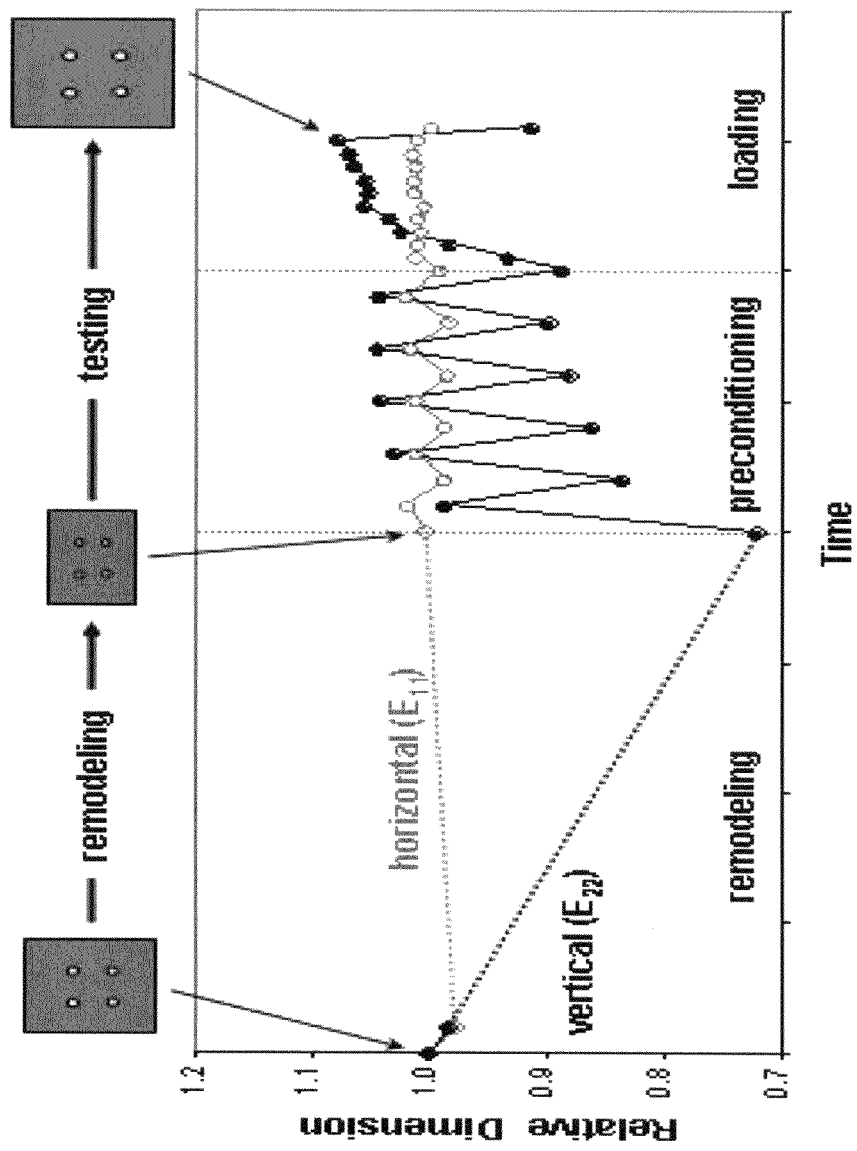
FIG. 3—Fibroblast populated fibrillar collagen gels for biomechanical testing.

Biomechanical Stiffening Changes Induced in Collagenous Tissues by Cross-Linking by Nitrite In order to study the biomechanical stiffening changes that can be induced in collagenous tissues by cross-linking by nitrite, the following study was undertaken. FIG. 3 provides a diagram and average deformation data showing the phases of the experiment for a uniaxially constrained gel. Initially square fibroblast-populated collagen gels were cast and allowed to polymerize for 2 hrs. Markers were painted on the gel surface to allow tracking of deformation in the central region during the remainder of the experiment. For the next 72 hrs (remodeling phase), spontaneous contraction of the gel by the fibroblasts resulted in vertical compaction (dotted black line), while applied weights prevented compaction in the horizontal direction (dotted gray line). At 72 hrs, the gel was mechanically tested. First, the gel was loaded and unloaded several times (i.e. generally 5 cycles) until the response stabilized (preconditioning phase). Then, the gel was loaded in a series of smaller steps and the response quantified (loading phase). During mechanical testing, deformations were much larger in the unconstrained, remodeled vertical direction (black line) than in the constrained, unremodeled horizontal direction (gray line).

Effects of Cross-Linking Porcine Cornea Using β-Nitro Alcohols

Figure 13:
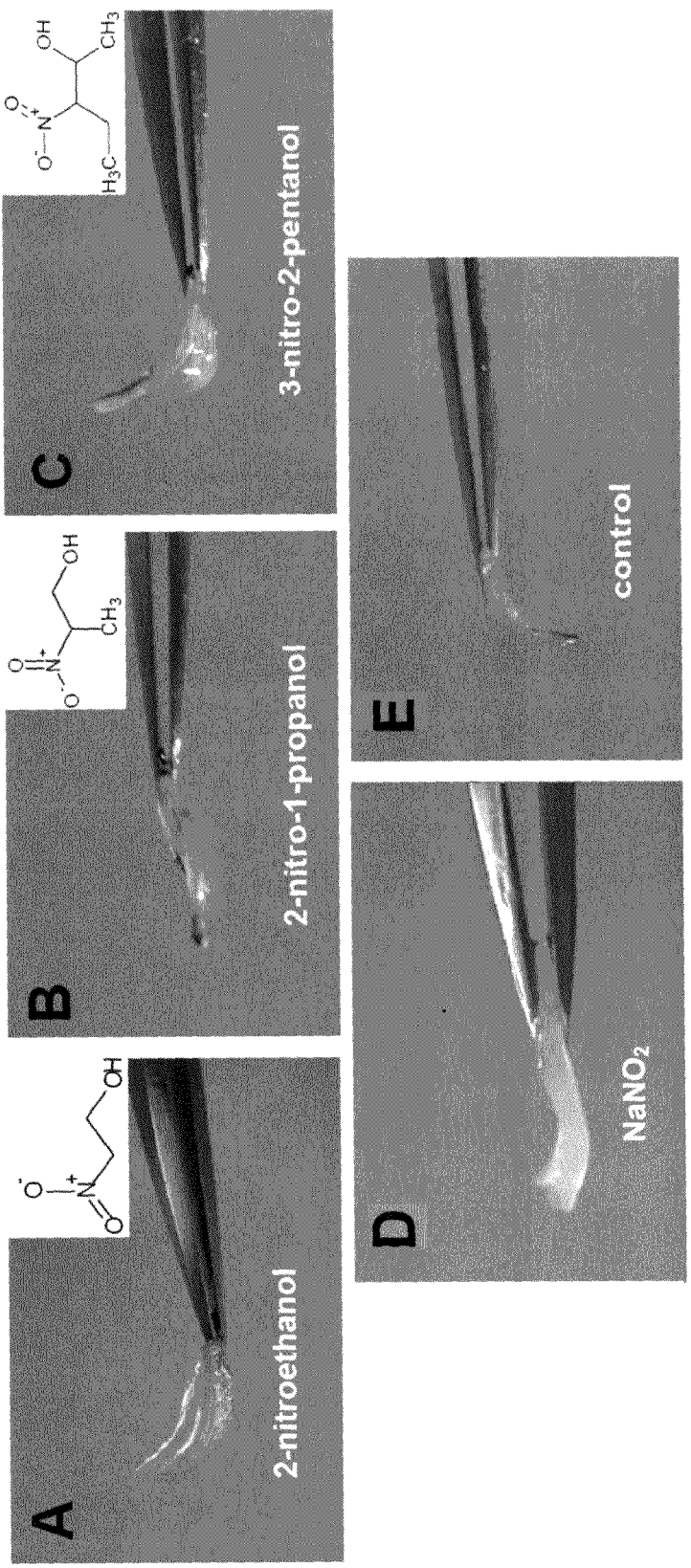
FIG. 13—Stiffening effects in corneal tissue induced by reaction with β-nitro alcohols.

These are the results of studies dealing directly with cross-linking of corneoscleral tissue. FIG. 13 illustrates the gross effects of cross-linking porcine cornea using β-nitro alcohols. These images were taken from tissues cross-linked with nitrite and the β-nitro alcohols 2-nitroethanol, 2-nitro-1-propanol, and 3-nitro-2-phenol, for 48 hrs. FIGS. 14(A-E) shows treated porcine corneal strips. Fresh porcine corneal strips and corneoscleral complexes were obtained within 6 hrs of sacrifice and incubated at 37° C. in buffered solutions (pH 7.4) containing 20% Dextran (T500) and either 100 mM NaNO$_2$ or 100 mM of one each of the β-nitro alcohols. After 48 hrs, the following images were obtained. FIGS. 13 (A and C) A dramatic stiffness change is induced by 2-nitroethanol and 3-nitro-2-pentanol when handled with a forceps. FIGS. 13 (B and D)

An intermediate effect is seen with 2-nitro-1-propanol and NaNO$_2$. FIG. 13 (E) Control cornea show very little stiffness. FIG. 13 illustrates the preserved transparency of the cornea treated with β-nitro alcohols, note yellow tint in 2-nitroethanol treated cornea. This observation raised a concern that cross-linking using this compound may induce negative effects on an individuals' blue light perception. At 100 mM concentration, a significant yellowing effect was observed using 2-nitroethanol, a similar but much less dramatic effect was seen for 2-nitro-1-propanol, and no yellowing effect was observable using 3-nitro-2-pentanol. As such, the effects on corneal light transmission induced by cross-linking with β-nitro alcohols was evaluated using a method adopted from Dillon et al 2004.

Following a 96 hrs incubation period at 10 mM, the corneoscleral complexes were mounted between 2 pieces of quartz, previously determined to have no ultraviolet absorption. This cross-linking regimen was chosen because the yellowing effect for 2-nitroethanol was profound at 100 mM making it impossible to obtain an absorption spectra at this level of cross-linking. Further, it represents a target level of cross-linking as determined by thermal shrinkage temperature. The tissue cross-linking effects induced by these conditions are commensurate with those reported for UV/riboflavin crosslinking and as such represent a level of cross-linking that would be predicted to have therapeutic value. The sample was then mounted in a vertical, adjustable stage apparatus specifically designed to accommodate a PC 1000 Fibre Optic Spectrometer (Ocean Optics, Inc.). A xenon lamp was used as a light source and was connected to the upper half of the stage. The lower half was connected to a high sensitivity CCD mounted on a card which is installed in a PC computer. The CCD array detector captures a full wavelength spectrum (i.e. 200-1000 nm).

The absorption spectrum for each sample was recorded and exported into Microcal Origin 6.1 for processing. Correction of the absorption spectra for light scattering (i.e. Rayleigh and Tyndall) was then performed as described by Dillon et al (2004). The scattering component was subtracted from the observed absorption spectrum by first fitting the scattering (non-absorption) portion of the spectrum (e.g. 700-800 nm) to the formula $A=a\lambda^b$, where A is the absorbance, $\lambda$ is the wavelength, b is the order of the relationship between absorbance and wavelength, and a is a constant. The background signal due to scattering for all other wavelengths is then estimated using the coefficients determined from the fit. These values are then subtracted from the spectrum to generate the true absorption spectrum. After scatter correction, the transmission spectrum for each absorption spectrum was calculated according to the Beer-Lambert law ($T=10^{-A} \times 100\%$), where T is the transmission and A is the absorbance at each wavelength. Finally, the effects on blue light transmission was determined by integrating the transmission spectra from 400-500 nm. A percent decrease was then calculated with respect to the area calculations using control samples.

A modest decrease in light transmission was noted for each compound. Decreased transmission was greatest for 2-nitroethanol, followed by 2nprop, and 3n2pent. Integration of the 400-500 nm blue light region revealed decreases of 3.6%, 1.5%, and 1.0%, for 2-nitroethanol, 2nprop, and 3n2pent, respectively (FIG. 15). The tinting can be avoided by using other β-nitro alcohols such as 2-nitro-1-propanol or 2-nitro-1-pentanol, both of which produce shifts in Ts without producing yellowing.

Shrinkage Temperatures of Porcine Cornea and Porcine and Human Sclera Cross-Linked with β-Nitro Alcohols Shrinkage temperature ($T_s$) of porcine cornea (FIG. 16) and porcine and human sclera (FIGS. 17 and 18) cross-linked with 2-nitroethanol. Fresh porcine corneal/sclera and human eye bank scleral strips (10×4 mm) were taken from the superior-inferior axis (cornea) and radially (sclera) and reacted with various concentrations of nitrite related agents (1-100 mM) for 24-96 hrs at 37° C. in 20% Dextran (T500), 0.2M $NaH_2PO_4/Na_2HPO_4$ (pH7.4). Following reaction, thermal shrinkage temperature analysis was performed (Table 4). Several compounds were studied including $NaNO_2$, 2-nitroethanol, 2-nitro-1-propanol, 3-nitro-2-pentanol, 2-nitrophenol, 2-nitroethane, 2-aminoethanol, isopentyl nitrite, DPTA/NO, DETA/NO, and urea, a nitrous acid trap.

Figure 16:
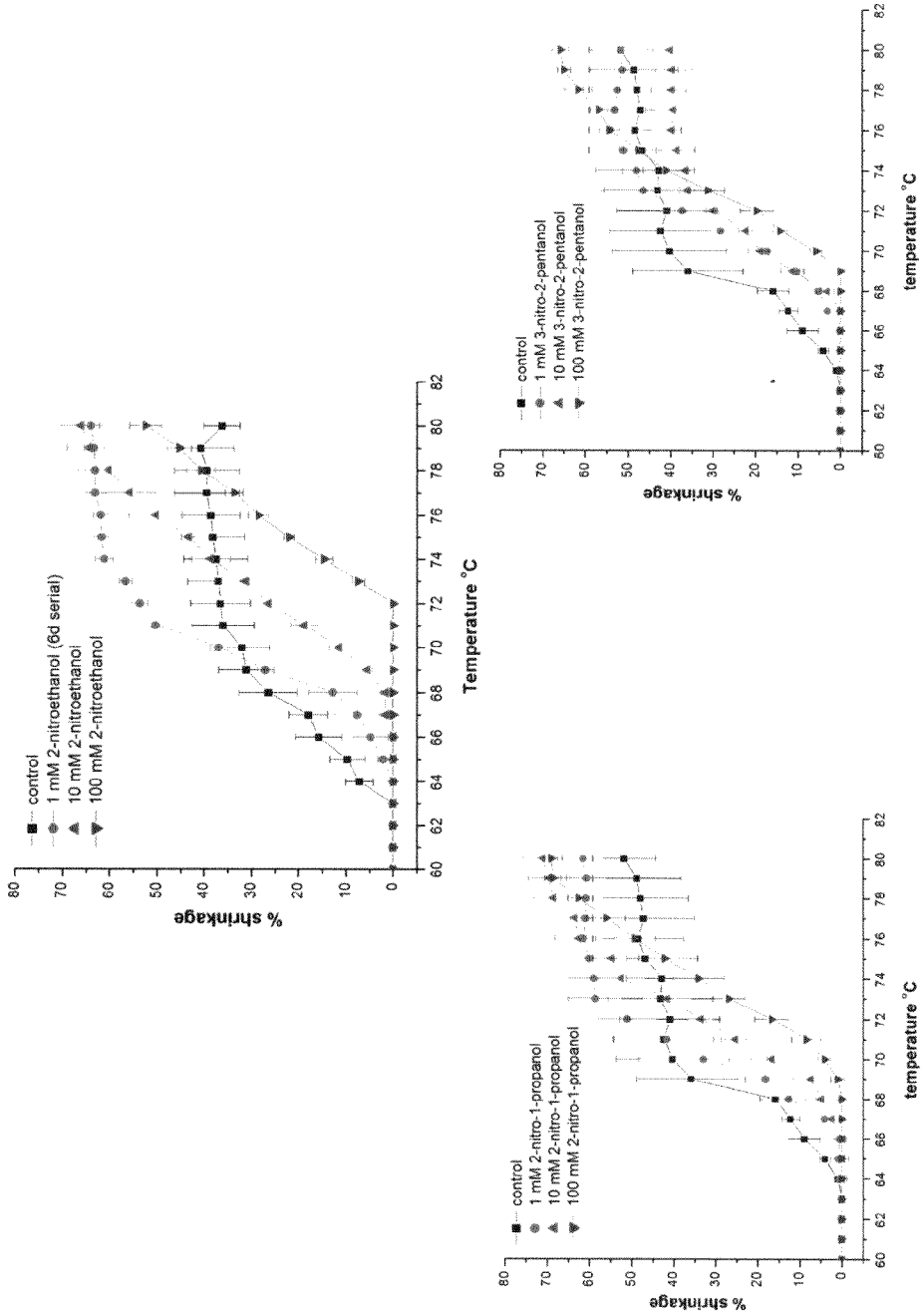
Figure 18:
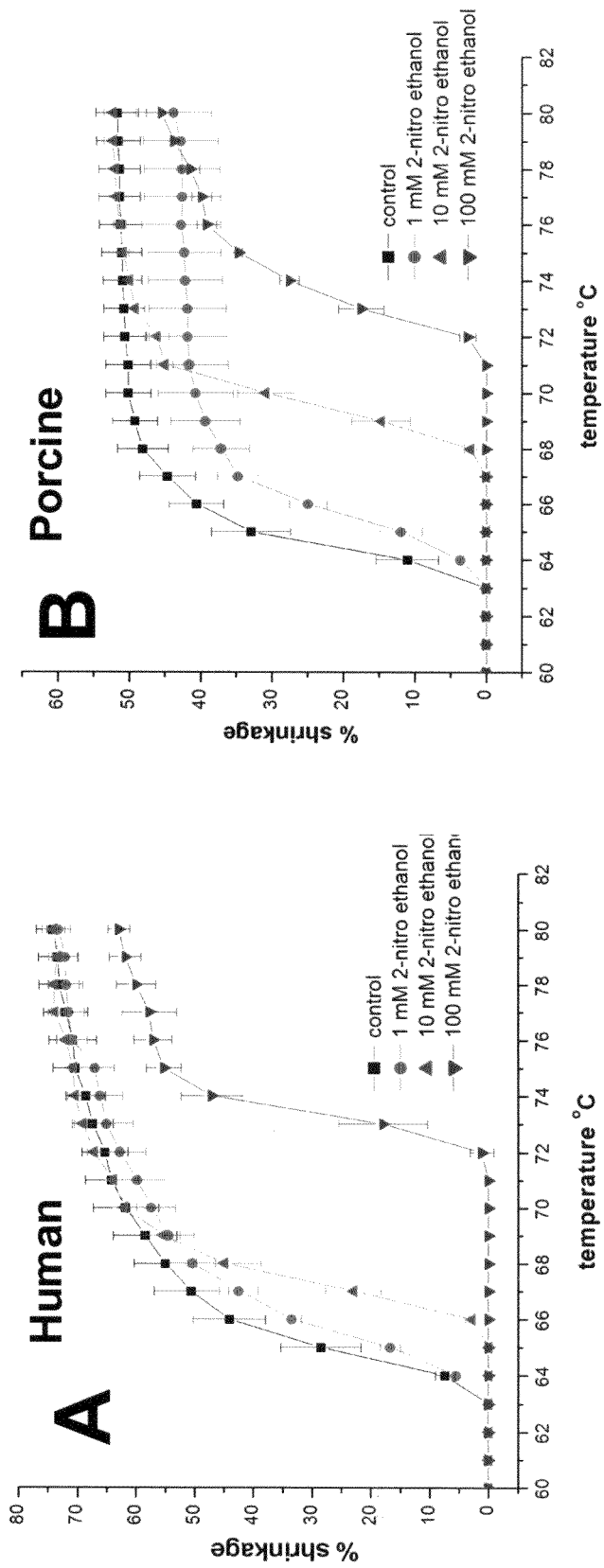

Controls displayed an onset of $T_s$ at 63° C. consistent with published data from the UVR group. $T_s$ onset were shifted 1-2° C. at 1 mM (serially applied over 6 days), 5° C. at 10 mM, and 8° C. at 100 mM 2-nitroethanol in porcine corneas (FIG. 16). These levels of cross-linking compare favorably with UVR reported $T_s$ onset values (5° C. shift). $T_s$ of porcine sclera are comparable to $T_s$ determined for porcine cornea with a maximal increase of $T_s$ of 8° C. at 100 mM 2-nitroethanol. Two human donor globes were used in order to confirm the effects of 2-nitroethanol in human tissue. As shown in FIG. 18, human samples similarly treated showed a similar degree of shift in $T_s$ as compared to porcine tissue, demonstrating a correlation between cross-linking porcine and human tissues. In addition, control human sclera showed similar $T_s$ values to porcine although the total percent shrinkage was higher. These shifts in $T_s$ indicate that nitro technology cross-links corneoscleral tissues.

Figure 19:
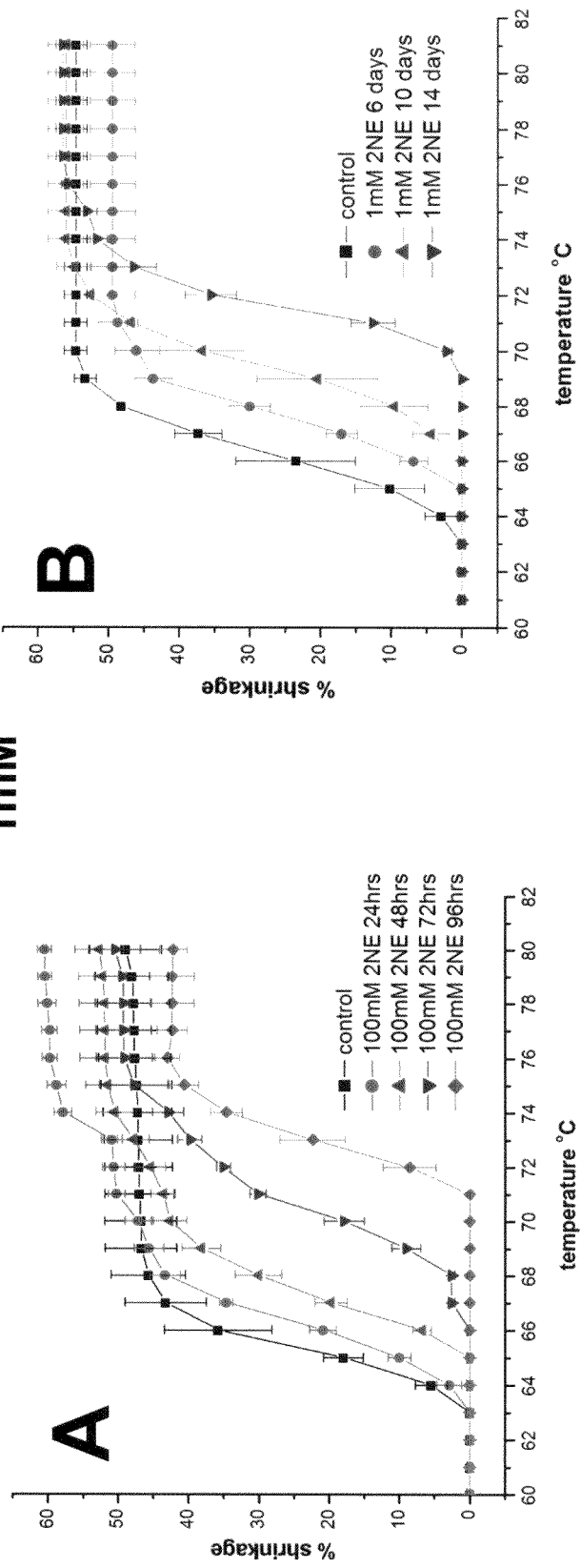

Time related shrinkage temperature curves changes using 2-nitroethanol on porcine sclera are illustrated in FIG. 19. FIG. 19A. The graph shows time dependent shifts in $T_s$ from porcine sclera cross-linked with 100 mM 2-nitroethanol over the course of 96 hrs (time dependent effect). That is, a longer incubation results in a higher temperature of shrinkage onset indicating increased cross-linking. A slightly different kinetic experiment was also performed using 2-nitroethanol at a concentration of 1 mM (FIG. 19B). In this case, the incubation was handled in a slightly different manner than the other experiments. For this study, the incubation solution containing the 1 mM 2-nitroethanol was exchanged daily for the duration of reaction. This was performed in order to replenish any of the reacted compound, maintaining a 1 mM concentration over the duration of exposure. As shown in FIG. 19B, a time dependent shift in $T_s$ was observed using a 1 mM concentration of 2-nitroethanol with shifts in $T_{50}$ of 1.3, 3.2, 5.4° C., at 6, 10 and 14 days, respectively. This concentration, by contrast, when reacted without exchange of the incubation fluid, did not induce a significant shift in $T_s$ after 4 days (FIG. 17A). Further, in FIG. 20, using a 1 mM 2-nitroethanol concentration, the incubation solution was changed daily over the course of 10 days and compared to Ts changes produced through incubating with 10 mM 2-nitroethanol over 4 days and 100 mM 2-nitroethanol over 3 days without changing the solution. This graph FURTHER indicates that comparable degrees of cross-linking can be achieved through modulation of reagent concentration and time of exposure. In other words, a relatively lower concentration of 2-nitroethanol (i.e. 1 mM) through serial applications (i.e. changing incubation fluid daily) can induce changes comparable to those observed using higher concentrations (i.e. 10 mM) for shorter time periods (i.e. 4 days). Simply using 1 mM 2-nitroethanol for 4 days without replacing the incubation solution did not produce a shift in Ts in porcine cornea or sclera.

TABLE 4

Thermal shrinkage temperature changes induced in porcine (and human) scleral strips by reaction with β-nitro alcohols and related agents.

| Compound/condition | reagent concentration (mM) | $T_i$* | $T_{50}$† | $T_{50}\Delta$‡ | p-value (for $T_{50}$) |
|---|---|---|---|---|---|
| 2-nitroethanol | 100 | 70.7 | 73.7 | 8.4 | 0.000 |
|  | 10 | 67.2 | 69.8 | 4.5 | 0.000 |
|  | 1 | 62.9 | 65.7 | 0.4 | NS |
| 2-nitro-1-propanol | 100 | 69.5 | 72.7 | 7.4 | 0.000 |
|  | 10 | 64.4 | 67.5 | 2.2 | 0.013 |
|  | 1 | 63.0 | 66.0 | 0.7 | NS |
| 3-nitro-2-pentanol | 100 | 68.3 | 70.7 | 5.4 | 0.001 |
|  | 10 | 65.3 | 67.7 | 2.4 | 0.006 |
|  | 1 | 62.5 | 66.2 | 0.9 | NS |
| 2-nitrophenol | 100 | 62.9 | 66.0 | 0.7 | NS |
|  | 10 | 62.3 | 65.6 | 0.3 | NS |
|  | 1 | 62.2 | 65.2 | -0.1 | NS |
| 2-nitroethane | 100 | 62.5 | 65.3 | 0 | NS |
|  | 10 | 62.5 | 65.4 | 0.1 | NS |
| 2-aminoethanol (ethanolamine) | 100 | 64.3 | 67.9 | 2.6 | 0.011 |
| Control porcine sclera (4° C.) |  | 62.9 | 65.3 |  |  |
| Control human sclera (4° C.) |  | 61.2 | 66.0 |  |  |

TABLE 4-continued

Thermal shrinkage temperature changes induced in
porcine (and human) scleral strips by reaction with β-nitro
alcohols and related agents.

| Compound/condition | reagent concentration (mM) | $T_i$* | $T_{50}$† | $T_{50}\Delta$‡ | p-value (for $T_{50}$) |
|---|---|---|---|---|---|
| Human sclera | 100 | 71.7 | 73.5 | 7.5 | 0.000 |
| 2-nitroethanol | 10 | 64.4 | 68.2 | 2.2 | 0.026 |
|  | 1 | 60.8 | 66.3 | 0.3 | NS |

Incubation solution includes 20% Dextran (T500) and 0.2M $NaH_2PO_4/Na_2HPO_4$ buffer pH 7.4 and 37° C. unless otherwise indicated. Incubation time was 96 hrs unless otherwise indicated.
Temperatures are indicated in ° C. $T_{50}$ for each condition was compared to control values (Student's t-test) in order to determine p-values for statistical significance.
Each value is the average of a minimum of 3 independent determinations.
*$T_i$ = temperature at 1% absolute shrinkage,
†$T_{50}$ = temperature at 50% of maximal shrinkage (or maximal rate of shrinkage change),
‡$T_{50}$ Δ = change in 50% shrinkage temperature compared to control.
All values were compared to porcine controls except for studies using human sclera and 2-nitroethanol.

Additional β-nitro alcohols related to 2-nitroethanol were also tested for scleral cross-linking efficacy. In addition to 2-nitroethanol, there was 2-nitro-1-propanol, 3-nitro-2-pentanol, and 2-nitrophenol. Of these, the short chain aliphatic compounds were shown to be effective cross-linking agents. 2-nitroethanol showed the greatest efficacy, shifting the $T_{50}$ by 8.5° C. at 100 mM concentration in porcine sclera and 7.5° C. in human sclera at 96 hrs of incubation (FIG. 18). This effect was not blocked by addition of equimolar urea (Table 5). 2-nitro-1-propanol (FIG. 17B) and 3-nitro-2-pentanol (FIG. 17C) showed cross-linking efficacy as well, with a $T_{50}$ shift for 2-nitro-1-propanol and 3-nitro-2-pentanol of 7.4° C. and 5.4° C., respectively. All three of these short chain aliphatic compounds showed a concentration dependent effect. Of note, 2-nitroethanol appears to have the greatest propensity to induce tissue yellowing. This appears to be a concentration dependent effect with the order of greatest yellowing in decreasing order: 2-nitroethanol, 2-nitro-1-propanol, and 3-nitro-2-pentanol. Very little yellowing was noted for any of the samples reacted at 10 mM.

No shift in $T_s$ is noted at 1 mM concentrations of either compound. This is similar to 2-nitroethanol in which shifts in $T_s$ at 1 mM could only be produced through serial application (i.e. daily changing of incubation solution) over the course of several days. The higher concentrations produce shifts in $T_s$ somewhat less than those found using 2-nitroethanol.

Several compounds were found to be ineffective as cross-linking agents. 2-nitrophenol, an aromatic β-nitro alcohol, produced very little shift in $T_s$ (FIG. 17D). 2-aminoethanol, the (3-amino alcohol corresponding to 2-nitroethanol, also produced only a marginal shift in $T_s$ (Table 1). 2-nitroethane, the nitroalkane corresponding to 2-nitroethanol, did not shift the $T_s$ to any extent (FIG. 21) (Table 4), indicating that the presence of the alcohol group was an important moiety in these reactions.

The results from cross-linking using glutaraldehyde and formaldehyde allow for a comparison to be made with this prototype chemical cross-linking agent. At moderate levels of $T_{50}$ shift (i.e. ~4° C.), glutaraldehyde was approximately 10× more potent as a cross-linking agent that 2-nitroethanol, producing a 3.6° C. shift at 1 mM concentration versus 4.5° C. shift at 10 mM concentration for 2-nitroethanol (see Table 5 and Table 4 respectively).

(Table 5) Previous studies have indicated that although the reaction with free nitrite at neutral pH can result in collagen cross-linking, the effects are slow, taking on the order of weeks. Furthermore, these cross-linking effects were shown to be facilitated by reacting under acidic conditions Paik DC, "Nitrite induced cross-linking alters remodeling and mechanical properties of collagenous engineered tissues". Connect T is Res. 47:163-76. In the present study, the effects of pH on the nitrite induced cross-linking were studied by reacting at three different pH values, 3, 5, and 7.4. At 96 hours, no effect was seen at pH 7.4. However, at pH 3 and 5, approximately equal shifts in $T_s$ were observed. Acid alone in the absence of $NaNO_2$ destabilized the tissues and resulted in a downward shift in $T_s$ (data not shown). The fact that acidification of $NaNO_2$ would increase cross-linking suggested that nitrosation could be involved Williams D L H. Nitrosation Reactions and the Chemistry of Nitric Oxide. Amsterdam, The Netherlands: Elsevier B.V.; 2004:1-43.

However, additional experiments did not support this claim. Equimolar urea a well known nitrous acid trapping agent Fitzpatrick J, et. al, "Comparison of the reactivity of nine nitrous acid scavengers". J Chem Soc Perkin Trans II. 1984:927-32., was unable to block the cross-linking effect by $NaNO_2$ at pH 3. In addition, studies using the nitrite ester isopentyl nitrite at neutral pH, an effective nitrosating agent, did not result in a shift in $T_s$ (FIG. 22). In these experiments, because isopentyl nitrite has poor solubility in water, a small facilitating amount of an organic solvent was added to increase solubility. Both ethanol and DMSO were used for this purpose, but neither condition resulted in changes in T. Finally, recent studies by Kong et al (2006) have shown that NO donors of the diazeniumdiolate class can result in nitrosation of peptide amide moieties resulting in deamidation, Kong L, Saavedra J E, Buzard G S, et al. "Deamidation of peptides in aerobic nitric oxide solution by a nitrosative pathway". Nitric Oxide. 2006; 14(2):444-51. Thus, we also tested these compounds for cross-linking efficacy. At neutral pH, DPTA/NO with a t/2=3 hrs was reacted for 24 hrs and DETA/NO with a t/2=30 hrs was reacted for 96 hrs. Neither compound was able to shift $T_s$ parameters (FIGS. 23 A and B).

TABLE 5

Thermal shrinkage temperature changes induced in
porcine sclera by reaction with acidified $NaNO_2$, nitrosating
agents, aldehydes, and other agents.

| Compound/condition | reagent concentration | T50 | T50 Δ | p-value (for T50) |
|---|---|---|---|---|
| $NaNO_2$ pH 3 | 100 mM | 69.3 | 4.0 | <.01 |
| $NaNO_2$ pH 5 | 100 mM | 67.3 | 2.0 | <.01 |
| $NaNO_2$ pH 7.4 | 100 mM | 65.7 | 0.4 | NS |
| $NaNO_2$ 100 mM pH 3 | 100 mM urea | 65.6 | 0.3 | NS |
|  | 10 mM urea | 69.7 | 4.4 | <.01 |
|  | 1 mM urea | 70.1 | 4.8 | <.01 |
| Isopentyl nitrite (1% DMSO) | 100 mM | 65.4 | 0.1 | NS |
| DPTA/NONO (24 hrs reaction) | 100 mM | 66.2 | 0.9 | NS |
|  | 10 mM | 66.4 | 1.1 | NS |
| DETA/NONO (96 hrs reaction) | 100 mM | 65.5 | 0.2 | NS |
| Glutaraldehyde | 1 mM | 68.9 | 3.6 | <.01 |
| Formaldehyde | 1 mM | 67.7 | 2.4 | <.01 |
| Ethanol | 100 mM | 65.2 | −0.1 | NS |
| DMSO | 1% | 65.0 | −0.3 | NS |

TABLE 5-continued

Thermal shrinkage temperature changes induced in porcine sclera by reaction with acidified NaNO$_2$, nitrosating agents, aldehydes, and other agents.

| Compound/condition | reagent concentration | T50 | T50 Δ | p-value (for T50) |
|---|---|---|---|---|
| Control porcine sclera (4° C.) | | 65.3 | | |
| Control human sclera (4° C.) | | 66.0 | | |

Incubation solution includes 20% Dextran (T500) and 0.2M NaH$_2$PO$_4$/Na$_2$HPO$_4$ buffer pH 7.4 and 37° C. unless otherwise indicated.
Incubation time was 96 hrs unless otherwise indicated.
Temperatures are indicated in ° C. T$_{50}$ for each condition was compared to control values (Student's t-test) in order to determine p-values for statistical significance. Each value is the average of a minimum of 3 independent determinations.
*T$_i$ = temperature at 1% absolute shrinkage,
†T$_{50}$ = temperature at 50% of maximal shrinkage (or maximal rate of shrinkage change),
‡T$_{50}$ Δ = change in 50% shrinkage temperature compared to control. All values were compared to porcine controls.

A cytotoxicity study was undertaken to obtain an impression of the level of cellular tolerance to these compounds. For pilot experiments ARPE-19 cells were used. This is an immortal human retinal pigment epithelial cell line commonly used for experiments related to macular degeneration. In these pilot studies, the ARPE-19 cells serve as a surrogate for cytotoxicity experiments. Primary cultures of bovine corneal endothelial cells were also used in the cytotoxicity studies described. Bovine corneal cells have more direct relevance for evaluating potential cytotoxic effects during cross-linking of living eye tissue.

ARPE-19 cells were grown to 80% confluence in 96 well tissue culture plates. The cells were then exposed to varying concentrations of NaNO$_2$ and 2-nitroethanol in their culture medium and evaluated for cell death using trypan blue (TB) staining (0.4% for 5 min) after 24 hrs. FIG. 24 shows the treated cells. FIG. 24(A) shows the morphology of control cells which did not stain positive with TB. A threshold of toxicity was found for cells exposed to 10 mm 2-nitroethanol. FIG. 24(D) shows that all of the cells took up TB in the 10 mM 2-nitroethanol group. FIG. 24(B) shows that no TB was taken up by cells at 1 mM 2-nitroethanol. FIG. 24(C) shows that even high levels of NaNO$_2$ (i.e. 100 mM) were tolerated by cells. These experiments indicate that there is a cytotoxic threshold for 2-nitroethanol that is between 1-10 mM. It appears that even millimolar levels of 2-nitroethanol can be tolerated by living cells.

Bovine corneal cells have are more directly relevant for the evaluation of potential cytotoxic effects during cross-linking of living eye tissue. As such, primary bovine corneal cells were used in cytotoxicity studies of β-nitro alcohols.

After growing in 96-well plates and with cells at 80-90% confluence, compounds of interest were added into the culture medium at a range of concentrations (0.001-1%). Following a 48 hrs incubation period, a cell suspension was obtained by trypsinization and dead cells were stained using 0.4% trypan blue for 5 min. The live/dead cells were then counted using a hemocytometer and the dead cell percent calculated. Three wells were used for each condition. A similar protocol was performed to evaluate the degree of apoptosis and necrosis, utilizing annexin V and propidium iodide staining according to the manufacturer's protocol (Molecular Probes, Inc.).

The toxicity levels vary between different β-nitro alcohols, wherein the highest tolerated level of 2-nitroethanol and 3-nitro-2-pentanol is 2 mM and the highest tolerated level of 2-nitro-1-propanol is 0.75 mM (FIG. 25, Tables 1 and 2). Comparatively, at 1 mM concentration, T$_s$ for porcine cornea was shifted 1-2° C. when β-nitro alcohols were serially applied over 6 days (FIG. 16) and T$_s$ for porcine sclera was shifted 2-3° C. when serially applied over 10 days (FIG. 19). The cytotoxic threshold of the β-nitro alcohols compares favorably with other known ophthalmic agents (Table 3).

For example, genipin, a natural iridoid cross-linking agent derived from the gardenia plant, has been reported to exhibit low cytotoxicity. In cytotoxicity studies using human fibroblasts, tolerable levels of genipin (0.44 mM or 0.01%) were shown to be more than 100× greater than glutaraldehyde and more than 20× greater than epoxy. Sung, H. W., et al., "Feasibility study of a natural crosslinking reagent for biological tissue fixation," J. Biomed. Mater. Res. 1998; 42:560-567. By comparison with the genipin studies, these cytotoxicity studies use the same exposure time (i.e. 24-48 hrs) with retinal pigment epithelial cells (ARPE-19) and bovine corneal endothelial cells. As shown above and in Table 3, the tolerable level of 2-nitroethanol was comparable in ARPE-19 to those reported for genipin (1 mM or 0.0091% for 2-nitroethanol vs. 0.44 mM or 0.01% for genipin). In bovine corneal endothelial cells the tolerable level of 2-nitroethanol was greater than those reported for genipin (3 mM or 0.0273% for 2-nitroethanol). Based on these studies, it is believed that serial application using lower doses can produce cross-linking effects similar to those induced at higher concentrations for shorter incubation periods. This therapy may produce corneal cross-linking over a relatively long period (2-8 weeks) using a dose of drops that would produce a subtoxic stromal tissue level. For free nitrite the tolerable levels were at least 100× higher (100 mM) than genipin, indicating that these compounds are relatively well tolerated by cells. β-nitro alcohols have very favorable mutagenicity (Conaway, C. C., et al., 1991) and animal toxicity profiles (Jung, Y. S., et al., 2004). As such, they have been proposed for use in animal feeds in order to control food borne pathogens in ruminants and chickens where they exhibit bacteriostatic activity (Horrocks, S. M., et al., 2007). Nitrite, as a sodium salt, can be found in the typical American and European diet, where it is routinely used as a cured meat preservative (Walker, R., 1990).

Penetration through the corneal epithelium is an important consideration regarding the utility of any potential topical therapy. In order to obtain an initial impression regarding the ability of nitrite and related compounds to pass through the corneal epithelium the following experiment was undertaken, the results of which are illustrated in FIG. 5.

Adult porcine eyes were obtained within 12 hrs of sacrifice and submerged in solutions of 0, 10, 100 mM NaNO$_2$ and 100 mM NaCl buffered with 50 mM NaH$_2$PO$_4$/Na$_2$HPO$_4$ (pH 7.4) following bubbling with 100% Argon in order to limit the amount of potential nitrite auto-oxidation caused by oxygen. Penicillin/Streptomycin was added (10 ul/ml) to prevent bacterial overgrowth. After 24 hrs of incubation at 4° C., the aqueous humor was sampled for nitrite concentration using a modification of the Greiss colorimetric assay. No nitrite was detected in either the buffer control or the 100 mM NaCl control. Nitrite concentration in the aqueous humor was 35.5% of the incubation fluid in the 10 mM NaNO$_2$ sample and 62.8% in the 100 mM NaNO$_2$ sample. These results suggest that there may be a concentration dependent penetration of nitrite through the cornea.

Discussion

Recent studies indicate that collagen cross-linking through reactions with nitrite and related agents can induce corneal changes commensurate with UVR therapy. In addition, published toxicity/mutagenicity studies suggest a good safety profile for these agents. Thus, nitro technology could be used as an "eye drop alternative" to UVR treatment. There are several advantages to this alternative. First, if no UVA irradiation is necessary, this could lessen the degree of cytotoxicity. This could allow doctors the opportunity to offer cross-linking treatment to all individuals, even those with thin corneas <400 µm. Second, patients would experience less discomfort since epithelial debridement would not be necessary. Third, since the compound would be self-administered, patients would benefit from the ease of application and reduced costs. Fourth, a more complete cross-linking could be possible, since water soluble nitro compounds can diffuse easily through the corneal stroma. The UVR method cross-links only the anterior 200 µm of cornea which correlates with the depth of penetration of UVA irradiation into the riboflavin soaked cornea (Kohlhaas, M., et al., 2006). Fifth, multiple re-treatments would be possible with topical therapy which may not be the case for UVR treatment. Sixth, a dose modulation could supply an effect of controlled magnitude rather that the single effect currently produced with the UVR procedure.

Recent studies indicate that collagen cross-linking through reactions with nitrite and related nitro agents can induce corneal collagen changes commensurate with the UVA/riboflavin (UVR) therapy. Specifically, changes in thermal shrinkage temperature (a general measure of collagen cross-linking) induced in pig cornea/sclera and human sclera, are comparable to that reported for UVR treatment. In addition, preliminary cell toxicity studies and literature suggest a reasonable safety profile for these agents. Related nitro agents have very favorable mutagenicity (Conaway, C. C., et al., "Evaluation of secondary nitroalkanes, nitrocarbinols, and other aliphatic nitro compounds in the Ames *Salmonella* assay," *Mut. Res.* 1991; 261(3):197-207) and animal toxicity profiles (Jung, Y. S., et al., "Experimental use of 2-nitro-1-propanol for reduction of *Salmonella Typhimurium* in the ceca of broiler chicks," *J. Food Prot.* 2004; 67:1945-1947). As such they have been proposed for use in animal feeds in order to control food borne pathogens in ruminants and chickens where they exhibit bacteriostatic activity (Horrocks, S. M., et al., "Effects of short-chain nitrocompounds against *Campylobacter jejuni* and *Campylobacter coli* in vitro," *J. Food Sci.* 2007; 72(2):M50-M55). Finally, nitrite, as a sodium salt, can be found in the typical American and European diet, where it is routinely used as a cured meat preservative (Walker, R., "Nitrates, nitrites and N-nitrosocompounds: a review of the occurrence in food and diet and the toxicological implications," *Food Additives and Contaminants* 1990; 7(6):717-768).

Thus, nitro technology may find clinical utility as a topical corneal stiffening agent and could have a significant impact not only on the treatment of keratoconus (which affects younger individuals) but also on post-PRK and post-LASIK keratectasias, which are devastating complications of keratorefractive surgery. These latter mentioned keratectasias are now emerging as a significant long-term complication (5-10 years) of LASIK and PRK surgery of unknown epidemiologic proportions (Binder, et al., 2005). They are also the basis of many of today's PRK- and LASIK-related medical malpractice litigations in opthalmology and optometry.

The earliest work from Wollensak, Spoerl, and Seiler was reported in 1998. The initial studies were aimed at identifying methods useful for corneal collagen cross-linking and included riboflavin with light exposure, glutaraldehyde, formaldehyde, and other aldehyde sugars. Spoerl, E., et al., "Induction of cross-links in corneal tissue," *Exp. Eye Res.* 1998; 66:97-103; Spoerl, E. and Seiler, T., "Techniques for stiffening the cornea," *J. Refract. Surg.* 1999; 15:711-713. These studies were followed by reports which determined the cytotoxic dose of the treatment on corneal endothelial cells and keratocytes using in vitro cell culture (Wollensak, G., et al., "Corneal endothelial cytotoxicity of riboflavin/UVA treatment in vitro," *Ophthalmic. Res.* 2003; 35:324-328; Wollensak, G., et al., "Keratocyte cytotoxicity of riboflavin/UVA-treatment in vitro," *Eye* 2004; 18:718-722) and the rabbit as a test animal (Wollensak, G., et al., "Endothelial cell damage after riboflavin-ultraviolet-A treatment in the rabbit," *J. Cataract Refract. Surg.* 2003; 29:1786-1790; Wollensak, G., et al., "Collagen fiber diameter in the rabbit cornea after collagen crosslinking by riboflavin/UVA," *Cornea* 2004; 23:503-507). Simultaneously, studies were performed which examined biochemical properties of cross-linked corneal tissue. Basic studies examining thermal denaturation temperature (Spoerl, E., et al., "Thermomechanical behavior of collagen-cross-linked porcine cornea," *Opthalmologica* 2004; 218:136-140) and resistance to enzymatic digestion (Spoerl, E., et al., "Increased resistance of crosslinked cornea against enzymatic digestion," *Cur. Eye Res.* 2004; 29(1):35-40) indicated that the combination of UVA with riboflavin as a photosensitizer was effective in cross-linking corneal collagen lamellae. These studies were performed in conjunction with bio-mechanical testing which confirmed increases in Young's modulus (Wollensak, G. and Spoerl, E., "Collagen crosslinking of human and porcine sclera," *J. Cataract Refract. Surg.* 2004; 30:689-95; Kohlhaas, M., et al., "Biomechanical evidence of the distribution of cross-links in corneas treated with riboflavin and ultraviolet A light," *J. Cataract Refract. Surg.* 2006; 32:279-283). Such basic biochemical, biomechanical, and animal studies were then followed by in vivo experiments aimed at determining the potential usefulness of this treatment in the living human eye.

Several chemical cross-linking agents were tested previously by the UVR group in comparison studies with the UVR method and included glucose, ribose, glyceraldehyde, and glutaraldehyde. Of these, only glyceraldehyde and glutaraldehyde, (i.e. aldehydes) were found to produce a significant biomechanical effect (Wollensak, G. and Spoerl, E., 2004). Glutaraldehyde is a well known cross-linking agent used for tissue cross-linking of bioprosthetic heart valves and for tissue fixation prior to viewing by electron microscopy. Its utility as an in vivo cross-linking agent, however, is limited by its significant cytotoxic effects. This is true for several other effective yet toxic aldehyde cross-linking agents, such as formaldehyde and glycoaldehyde. Glyceraldehyde is a physiologic metabolic product, is generally considered non-toxic, and could also be potentially used for topical corneal cross-linking. Another class of cross-linking compounds that could have utility for in vivo cross-linking is the iridoid compounds, of which genipin is an example. Nimni, M. E., "Glutaraldehyde fixation revisited," *Journal of Long-Term Effects of Medical Implants* 2001; 11(3&4):151-161; Jayakrishnan, A. and Jameela, S. R., "Review: Glutaraldehyde as a fixative in bioprostheses and drug delivery matrices," *Biomaterials* 1996; 17:471-484.

This invention uses a nitrogen oxide-containing compound to cross-link collagen in collagenous tissue.

Non Enzymatic Cross-Linking of Collagen Tissue

There are two general types of collagen cross-linking: enzymatic and non-enzymatic. Enzymatic cross-linking occurs in distinct telopeptide and helical regions of the collagen molecule. The process is mediated by the enzyme lysyl oxidase and forms a number of borohydride reducible and nonreducible cross-links. Eyre, D. R., "Cross-linking in collagen and elastin," *Ann. Review Biochem.* 53:717-48 (1984); Bailey, A. J., "Glycation of collagen: the basis of its central role in the late complications of ageing and diabetes." *Mech. Ageing, Devel.*, 122:735-55 (2001).

Nonenzymatic cross-linking is thought to accumulate gradually over the course of a person's lifetime, resulting in the hallmark aging change of decreased solubility and increased resistance to enzymatic digestion. This process is especially deleterious because the formation of increasingly undigestible collagen will prevent its clearance by collagenases, further allowing for the accumulation of damaged proteins. Bailey, A. J., "Glycation of collagen: the basis of its central role in the late complications of ageing and diabetes." *Mech. Ageing, Devel.*, 122:735-55 (2001); Paul, R. G., and Bailey, A. J., "Glycation of collagen: the basis of its central role in the late complications of ageing and diabetes." *Int. J. Biochem. Cell Biol.* 28(12):1297-1310 (1996).

Collagen cross-linking via nonenzymatic glycation (NEG) has been implicated in the development of increased tissue stiffness. An additional and novel mechanism that may contribute to nonenzymatic human collagen cross-linking is through nonenzymatic nitrite (NEN) modification. Paik, D. C., et al., "The nitrite/collagen reaction: non-enzymatic nitration as a model system for age-related damage." *Con. Tis. Res.* 42(2):111-22 (2001). NEN of type I collagen results in an increased resistance to proteolytic digestion and alters the ultraviolet/visible absorption consistent with aging changes. Nitrite Several methods are known to induce nonenzymatic cross-linking of collagenous tissues. The best known of these include methods involving glutaraldehyde, sugar molecules such as glucose, ribose, glyceraldehyde, glycoaldehyde, rose bengal/white-light irradiation, and riboflavin with ultraviolet-A irradiation. The latter method, riboflavin/UVA has been used successfully in the treatment of keratoconus.

This invention is an alternative method of tissue cross-linking in the eye, that is, a reaction of collagen with the nitrite ion. Nitrite is a compound which has a significant history in the scientific literature. Nitrite, in the form of its sodium and/or potassium salt, has been used for several decades as a means of preserving and altering the qualities of meat and fish products in the process of curing. This processing is well known to the meat industry and is performed specifically to preserve meats destined for human consumption. The process prevents spoilage by *Clostridium botulinum*, the bacterium causing the disease known as botulism.

Nitrite reactions have been used to study the human aging process, since non-enzymatic collagen cross-linking is a hallmark change observed during the aging of numerous organ systems, including the eye, cardiovascular system, and skin. Nitrite reactions with collagen and collagenous engineered tissues result in the formation of non-enzymatic cross-linking and resultant tissue stiffening. Paik, D. C., et al., "Nitrite-Induced Cross-Linking Alters Remodeling and Mechanical Properties of Collagenous Engineered Tissues." *Connective Tissue Research*, 47:163-76 (2006). Although previous studies have viewed nitrite mediated collagen cross-linking as a potential mechanism in the development of human disease, this invention provides potential therapeutic benefit that intentional nitrite induced collagen cross-linking may have. This concept has been spurred by recent developments in the treatment of keratoconus. In this case, collagen cross-linking using riboflavin/UVA has been used to stabilize corneal collagen lamellae, preventing the untoward effects of progressive corneal thinning. Thus, this invention involves the application of nitrite induced cross-linking to the stiffening of collagen containing tissues for the purpose of stabilization with therapeutic intent.

The formation of reactive nitrogen species (RNS) and resultant nitrative and nitrosative damage is important in this invention. Reactions involving nitrite ion are a means through which nitrogen oxide exert effects on human tissues. Nitrite can act as a reactive substrate for an array of chemical reactions. At least three different reaction pathways are known to occur and have biological significance. First, nitrite can mediate nitrosation reactions under acidic conditions through the formation of nitrosonium ion ($NO^+$) and/or dinitrogen trioxide ($N_2O_3$) in acidic electrophilic addition. Kurosky, A., and Hofmann, T. "Kinetics of the reaction of nitrous acid with model compounds and proteins, and the conformational state of N-terminal groups in the chymotrypsin family." *Can. J. Biochem.* 50:1282-96 (1972); Zhang, Y. Y., et al., "Nitrosation of tryptophan residue(s) in serum albumin and model dipeptides." *J. Biol. Chem.* 271(24):14271-79. Second, oxometal complex formation by heme peroxidase/$H_2O_2$, or free Fe/$H_2O_2$ in Fenton-type reactions, can cause nitration through single electron transfer to nitrite, forming nitrogen dioxide ($NO_2$). Finally, hydroxyl radical (OH) and nitrogen dioxide ($NO_2$) can be produced through the photochemical decomposition of nitrite. Thus, nitrite can be involved in both nitrosation as well as nitration reactions.

Nitrites of the alkali and alkaline earth metals may be synthesized by reacting a mixture of nitric oxide and nitrogen dioxide with the corresponding metal hydroxide solution, as well as through the decomposition of the corresponding nitrate. Nitrites are also available through the reduction of the corresponding nitrates. Nitrites can be obtained from sources such as nitrous acid (as nitrosonium ion and/or dinitrogen trioxide); nitrosyl halides of the formula HalNO where Hal is a member of the group of fluorine, chlorine, bromine, iodine, or astatine; nitrosonium salts; alkyl nitrites; N-Nitrososulfonamides of the formula $RSO_2N(NO)R'$, where R and R' can be any organic substituent, such as an acetal, acid anhydride, alcohol, aldehyde, alkane, cycloalkane, alkene, cycloalkene, alkyl, alkylamine, alkyl halide, alkyne, cycloalkyne, allyl, amide, amine, annulene, arene, aryl halide, arylamine, aryne, carbinolamine, carboxylic acid, dicarboxylic acid, ether, hydrocarbon, imide, imine, ketone, lactam, lactone, peroxide, phenol, phenyl, polyamide, polyamine, polycyclic aromatic hydrocarbon, polycyclic hydrocarbon, saccharide, thiol, or thioester; tetranitromethane $C(NO_2)_4$; inorganic nitrates; nitrite with carbonyl group catalysts; nitrosyl carboxylates (acyl nitrites) of the formula RCOONO, where R has the same definition as previously disclosed; Fremy's salt $K_2[(SO_3)_2NO]$; and sulfur-nitroso compounds such as thionyl chloronitrite SOCIONO and thionyl dinitrite $SO(ONO)_2$.

Nitrite ion is also one of the many by-products of nitric oxide, and is known to accumulate in the anterior chamber of the eye during ocular inflammation and can be derived from cigarette smoking. It has been observed that nitrite reactions with the matrix proteins elastin and collagen produce damaging effects that mimic those observed in age- and smoking-related illnesses. Since human exposure to nitrite is increased by cigarette smoking, this reaction could explain the association between ocular degeneration and smoking. Paik, D. C. and Dillon, J., "The nitrite/alpha cristillin reaction: A possible mechanism in lens matrix damage." *Exp. Eye Res.*, 70:73-80 (2000).

However, in some cases collagen cross-linking is desirable as a treatment of certain conditions or to preserve tissue during transplantation as described herein.

Additional references relating to this invention include the following: Abraham, V. C., et al., "High content screening applied to large-scale cell biology," *Trends in Biotechnology* 2004; 22(1):15-22; Amano, S., et al., "Comparison of central corneal thickness measurements by rotating scheimpflug camera, ultrasonic pachymetry, and scanning-slit corneal topography," *Opthalmology* 2006; 113:937-941; Bailey, A. J., "Molecular mechanisms of ageing in connective tissues," *Mech. Aging Dev.* 2001; 122:735-55; Banse, X., et al., "Cross-link profile of bone collagen correlates with structural organization of trabeculae," *Bone* 2002; 31(1):70-76; Bednarz, J., et al., "Effect of three different media on serum free culture of donor corneas and isolated human corneal endothelial cells," *Br. J. Opthalmol.* 2001; 85:1416-1420; Brady, J. D. and Robins, S. P., "Structural characterization of pyrrolic cross-links in collagen using a biotinylated Ehrlich's reagent," *J. Biol. Chem.* 2001; 276(22):18812-18818; Chiou, A. G. Y., et al., "Clinical corneal confocal microscopy," *Survey of Opthalmology* 2006; 51(5):482-500; Eyre, D. R., et al., "Cross-linking in collagen and elastin," *Ann. Rev. Biochem.* 1984; 53:717-748; Lackner, B., et al., "Repeatability and reproducibility of central corneal thickness measurement with pentacam, orbscan, and ultrasound," *Optometry and Vision Science* 2005; 82:892-899; Lee, M. Y. and Dordick, J. S., "High-throughput human metabolism and toxicity analysis," *Current Opinion in Biotechnology* 2006; 17:619-627; McLaren, J. W., et al., "Corneal thickness measurement of confocal microscopy, ultrasound, and scanning slit methods," *Am. J. Opthalmol.* 2004; 137:1011-1020; Naor, J., et al., "Corneal endothelial cytotoxicity of diluted providone-iodine," *J. Cataract Refract. Surg.* 2001; 27:941-947; Sady, C., et al., "Advanced Maillard reaction and crosslinking of corneal collagen in diabetes," *Biochem. Biophys. Res. Com.* 1995; 214(3):793-797; Sell, D. R. and Monnier, V. M., "Structure elucidation of a senescence cross-link from human extracellular matrix," *J. Biol. Chem.* 1989; 264(36):21597-21602; Skinner, S. J. M., "Rapid method for the purification of the elastin cross-links, desmosine and isodesmosine," J. Chromatog. 1982; 229:200-204; Wollensak, G., et al., "Stress-strain measurements of human and porcine corneas after riboflavin-ultraviolet-A-induced cross-linking," *J. Cataract Refract. Surg.* 2003; 29:1780-1785.

What is claimed is:

1. A method of cross-linking collagen in a collagenous tissue comprising contacting the collagenous tissue with an amount of a nitrogen oxide-containing compound effective to cross-link the collagen in the collagenous tissue, wherein the nitrogen oxide-containing compound is a β-nitro alcohol.

2. The method of claim 1 wherein the collagenous tissue is in a subject.

3. The method of claim 1 or claim 2 wherein the collagenous tissue is cornea, sclera, skin, tendon, blood vessel, heart valve, bone, cartilage or other tendinous tissue.

4. The method of claim 3 wherein the collagenous tissue is cornea.

5. The method of claim 1 wherein the collagenous tissue is human cornea.

6. The method of claim 2 wherein the collagenous tissue is cornea and the subject is afflicted with keratoconus or keratectasia.

7. The method of claim 1 wherein the β-nitro alcohol is 2-nitro-1-pentanol.

8. The method of claim 1 wherein the β-nitro alcohol is 2-nitroethanol.

9. The method of claim 1 wherein the β-nitro alcohol is 2-nitro-1-propanol.

10. The method of claim 1 wherein the β-nitro alcohol is 3-nitro-2-pentanol.

11. The method of claim 1 wherein the β-nitro alcohol is selected from the group consisting of 2-nitro-1-pentanol, 2-nitroethanol, 2-nitro-1-propanol, 3-nitro-2-pentanol and combinations thereof.

12. The method of claim 1 wherein the β-nitro alcohol is in an aqueous solution having a pH of 3 to a pH of 10.

13. The method of claim 12 wherein the β-nitro alcohol is in an aqueous solution having a pH of 7.4.

14. The method of claim 1 wherein the β-nitro alcohol is in an aqueous solution comprising sodium phosphate, potassium phosphate, dextran, sodium chloride, potassium chloride, calcium chloride dihydrate, magnesium chloride hexahydrate, sodium acetate trihydrate, sodium citrate dehydrate, and balance water.

15. The method of claim 1 wherein the β-nitro alcohol is in an aqueous solution comprising 0 to 20 percent sodium phosphate by weight/volume, 0 to 20 percent potassium phosphate by weight/volume, and 0 to 20 percent dextran by weight/volume.

16. The method of claim 1 wherein the β-nitro alcohol is in an aqueous solution comprising 0.64% sodium chloride by weight/volume, 0.075% potassium chloride by weight/volume, 0.048% calcium chloride dihydrate by weight/volume, 0.03% magnesium chloride hexahydrate by weight/volume, 0.39% sodium acetate trihydrate by weight/volume, 0.17% sodium citrate dehydrate by weight/volume, and balance water.

17. The method of claim 1, wherein the β-nitro alcohol is in an aqueous solution and wherein the tonicity of the aqueous solution is from 1 milli-osmoles to 100 osmoles.

18. The method of claim 1 wherein the contacting of the β-nitro alcohol to the collagenous tissue is performed by intermittent administration of the nitrogen oxide-containing compound to the collagenous tissue for a duration of time effective to cross-link collagen.

* * * * *